(12) United States Patent
Liddicoat et al.

(10) Patent No.: US 7,186,264 B2
(45) Date of Patent: *Mar. 6, 2007

(54) METHOD AND APPARATUS FOR IMPROVING MITRAL VALVE FUNCTION

(75) Inventors: John R. Liddicoat, Sewickley, PA (US); Daniel C. Taylor, Brighton, MA (US); Richard B. Streeter, Winchester, MA (US); Steven B. Woolfson, Boston, MA (US); William E. Cohn, Chestnut Hill, MA (US); Todd F. Davenport, Andover, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/112,354

(22) Filed: Mar. 29, 2002

(65) Prior Publication Data

US 2002/0183838 A1 Dec. 5, 2002

Related U.S. Application Data

(63) Continuation-in-part of application No. 10/068,264, filed on Feb. 5, 2002, now Pat. No. 6,656,221.

(60) Provisional application No. 60/348,424, filed on Jan. 14, 2002, provisional application No. 60/339,481, filed on Oct. 26, 2001, provisional application No. 60/312,217, filed on Aug. 14, 2001, provisional application No. 60/283,820, filed on Apr. 13, 2001, provisional application No. 60/280,038, filed on Mar. 30, 2001, provisional application No. 60/279,974, filed on Mar. 29, 2001, provisional application No. 60/279,973, filed on Mar. 29, 2001.

(51) Int. Cl.
*A61F 2/24* (2006.01)

(52) U.S. Cl. .................... 623/2.37; 623/903; 623/904

(58) Field of Classification Search .............. 623/1.1, 623/1.16, 2.11, 2.37, 903, 904
See application file for complete search history.

(56) References Cited

U.S. PATENT DOCUMENTS 4,535,757 A 8/1985 Webster, Jr.

(Continued)

FOREIGN PATENT DOCUMENTS

DE 101 61 543 A1 6/2003

(Continued)

OTHER PUBLICATIONS

Buchanan, James W., Circumferential Suture of the Mitral Annulus for Correction of Mitral Regurgitation in Dogs, Veterinary Surgery, 1998, pp. 182-193.

(Continued)

*Primary Examiner*—Brian E. Pellegrino
(74) *Attorney, Agent, or Firm*—Pandiscio & Pandiscio

(57) ABSTRACT

A method and apparatus for reducing mitral regurgitation. The apparatus is inserted into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation and reduce mitral regurgitation.

19 Claims, 43 Drawing Sheets

U.S. PATENT DOCUMENTS

| | | | |
|---|---|---|---|
| 4,669,473 | A | 6/1987 | Richards et al. |
| 4,917,698 | A | 4/1990 | Carpentier et al. |
| 4,944,745 | A | 7/1990 | Sogard et al. |
| 5,061,277 | A | 10/1991 | Carpentier et al. |
| 5,092,889 | A | 3/1992 | Campbell, Jr. |
| 5,269,809 | A | 12/1993 | Hayhurst et al. |
| 5,332,402 | A | 7/1994 | Teitelbaum |
| 5,383,892 | A | 1/1995 | Cardon et al. |
| 5,389,091 | A | 2/1995 | Moorehead |
| 5,443,481 | A | 8/1995 | Lee |
| 5,462,530 | A | 10/1995 | Jang |
| 5,476,506 | A | 12/1995 | Lunn |
| 5,527,292 | A | 6/1996 | Adams et al. |
| 5,545,209 | A | 8/1996 | Roberts et al. |
| 5,562,620 | A | 10/1996 | Klein et al. |
| 5,569,201 | A | 10/1996 | Burns |
| 5,575,799 | A | 11/1996 | Bolanos et al. |
| 5,681,345 | A | 10/1997 | Euteneuer |
| 5,720,726 | A | 2/1998 | Marcadis et al. |
| 5,755,778 | A | 5/1998 | Kleshinski |
| 5,755,781 | A * | 5/1998 | Jayaraman ................ 623/1.16 |
| 5,800,495 | A | 9/1998 | Machek et al. |
| 5,800,526 | A | 9/1998 | Anderson et al. |
| 5,855,565 | A | 1/1999 | Bar-Cohen et al. |
| 5,911,732 | A | 6/1999 | Hojeibane |
| 5,957,949 | A | 9/1999 | Leonhardt et al. |
| 5,980,570 | A | 11/1999 | Simpson |
| 5,984,917 | A | 11/1999 | Fleischman et al. |
| 6,033,436 | A | 3/2000 | Steinke et al. |
| 6,051,020 | A | 4/2000 | Goicoechea et al. |
| 6,071,263 | A | 6/2000 | Kirkman |
| 6,086,599 | A | 7/2000 | Lee et al. |
| 6,090,136 | A | 7/2000 | McDonald et al. |
| 6,119,037 | A | 9/2000 | Kellogg et al. |
| 6,162,245 | A | 12/2000 | Jayaraman |
| 6,165,194 | A | 12/2000 | Denardo |
| 6,187,040 | B1 | 2/2001 | Wright |
| 6,210,432 | B1 | 4/2001 | Solem et al. |
| 6,241,746 | B1 | 6/2001 | Bosma et al. |
| 6,258,117 | B1 | 7/2001 | Camrud et al. |
| 6,277,107 | B1 | 8/2001 | Lurie et al. |
| 6,328,765 | B1 | 12/2001 | Hardwick et al. |
| 6,332,896 | B1 | 12/2001 | Hubbard et al. |
| 6,402,781 | B1 | 6/2002 | Langberg et al. |
| 6,419,696 | B1 | 7/2002 | Ortiz et al. |
| 6,537,314 | B2 | 3/2003 | Langberg et al. |
| 6,569,198 | B1 | 5/2003 | Wilson et al. |
| 6,585,716 | B2 | 7/2003 | Altman |
| 6,602,288 | B1 | 8/2003 | Cosgrove et al. |
| 6,648,874 | B2 | 11/2003 | Parisi et al. |
| 6,656,221 | B2 * | 12/2003 | Taylor et al. ............... 623/2.11 |
| 2001/0018611 | A1 | 8/2001 | Solem et al. |
| 2001/0044568 | A1 | 11/2001 | Langberg et al. |
| 2001/0052345 | A1 | 12/2001 | Niazi |
| 2002/0016628 | A1 | 2/2002 | Langberg et al. |
| 2002/0087173 | A1 | 7/2002 | Alferness et al. |
| 2002/0099431 | A1 | 7/2002 | Armstrong et al. |
| 2002/0103532 | A1 | 8/2002 | Langberg et al. |
| 2002/0103533 | A1 | 8/2002 | Langberg et al. |
| 2002/0151961 | A1 | 10/2002 | Lashinshi et al. |
| 2002/0169502 | A1 | 11/2002 | Mathis |
| 2002/0169504 | A1 | 11/2002 | Alferness et al. |
| 2003/0069636 | A1 | 4/2003 | Solem et al. |
| 2003/0083538 | A1 | 5/2003 | Adams et al. |
| 2003/0093148 | A1 | 5/2003 | Bolling et al. |
| 2003/0105520 | A1 | 6/2003 | Alferness et al. |

FOREIGN PATENT DOCUMENTS

| | | |
|---|---|---|
| EP | 756853 A1 * | 2/1997 |
| JP | 409322936 A | 12/1997 |
| WO | WO 98/22159 A2 | 5/1998 |
| WO | WO 00/62708 A | 10/2000 |
| WO | WO 01/00111 A1 | 1/2001 |
| WO | WO 01/54618 A1 | 8/2001 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/091908 A2 | 11/2002 |
| WO | WO 02/100240 A2 | 12/2002 |
| WO | WO 03/037171 A2 | 5/2003 |

OTHER PUBLICATIONS

Kerstetter, Kyle K. et al., Short-Term Hemodynamic Evaluation of Circumferential Mitral Annuloplasty for Correction of Mitral Valve Regurgitation in Dogs, Veterinary Surgery, 1998, pp. 216-223.

Beardow, Andrew W. et al., Chronic Mitral Valve Disease in Cavalier King Charles Spaniels: 95 Cases (1987-1991), JAVMA, vol. 203, No. 7, Oct. 1, 1993, pp. 1023-1029.

Davila, Julio C. et al., Circumferential Suture of The Mitral Ring, 18 pages.

Glover, Robert P. et al., The Treatment of Mitral Valve Insufficiency By The Purse-String Technique, The Journal of Thoracic Surgery, Jan. 1957, 14 pages.

Davila, Julio C. et al., Circumferential Suture of The Mitral Valve for the Correction of Regurgitation, The American Journal of Cardiology, Inc., Sep. 1958, 6 pages.

Buchanan, James W., Causes and Prevalence of Cardiovascular Disease, Current Veterinary Therapy XI, WB Saunders Co., 1992, 2 pages.

* cited by examiner

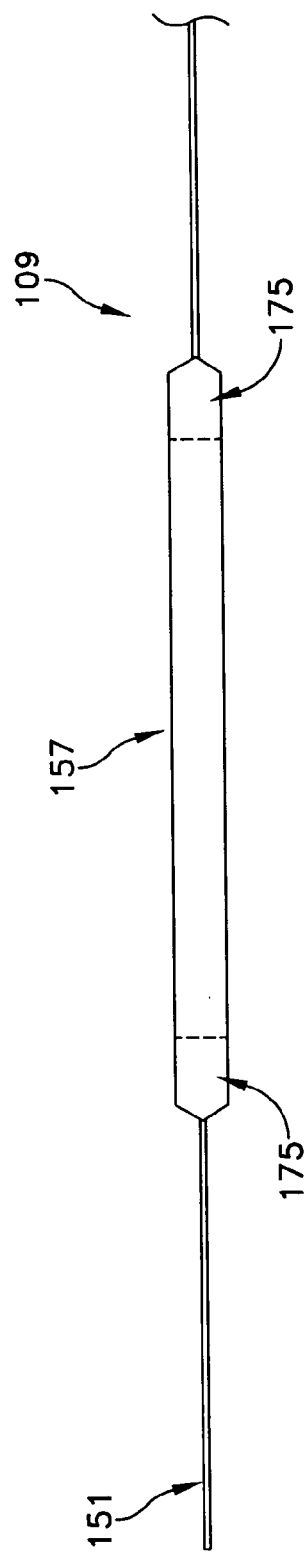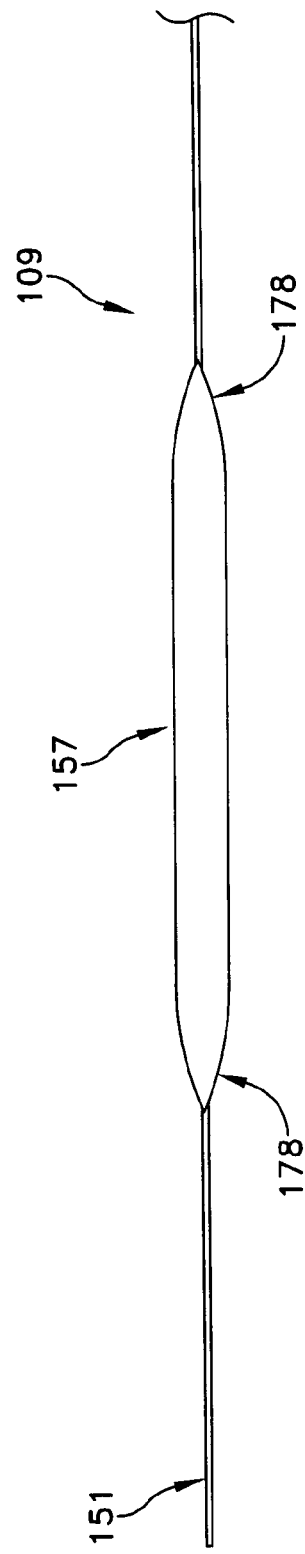

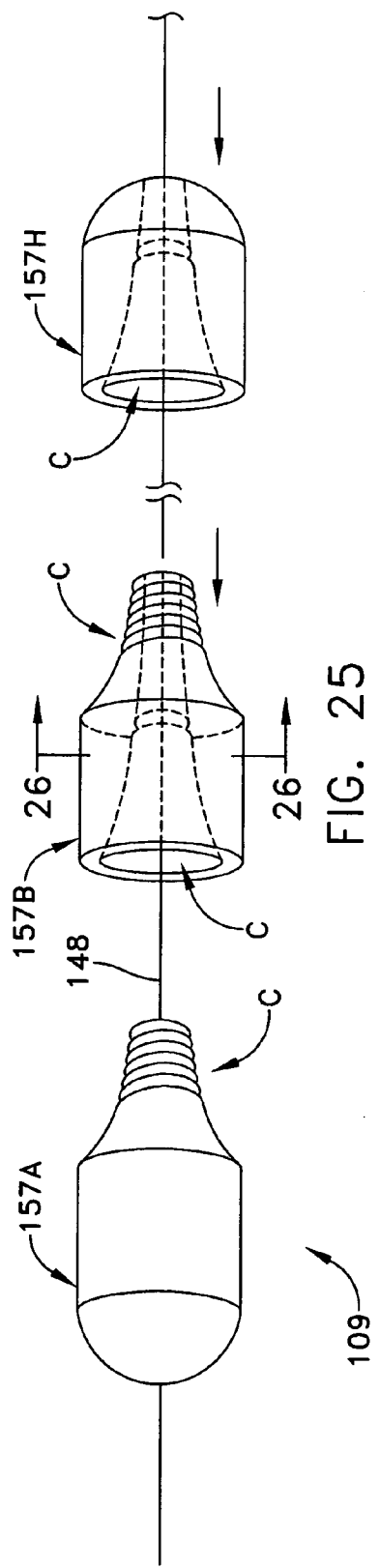
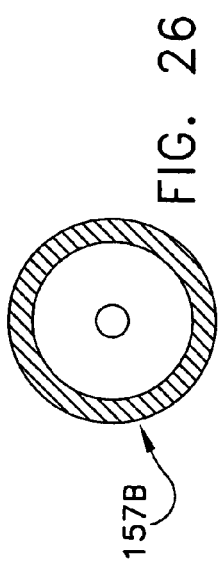
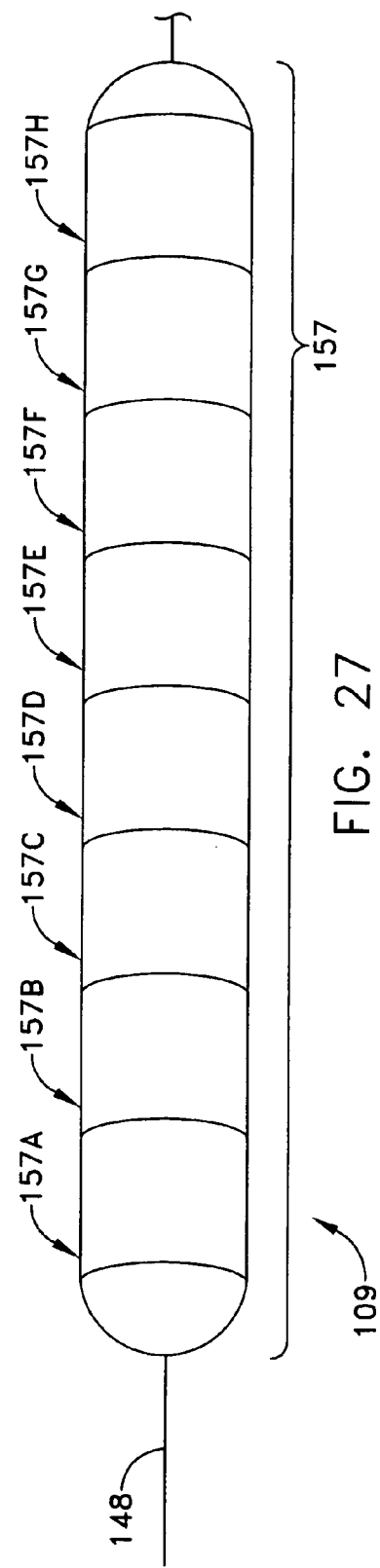
FIG. 25
FIG. 26
FIG. 27

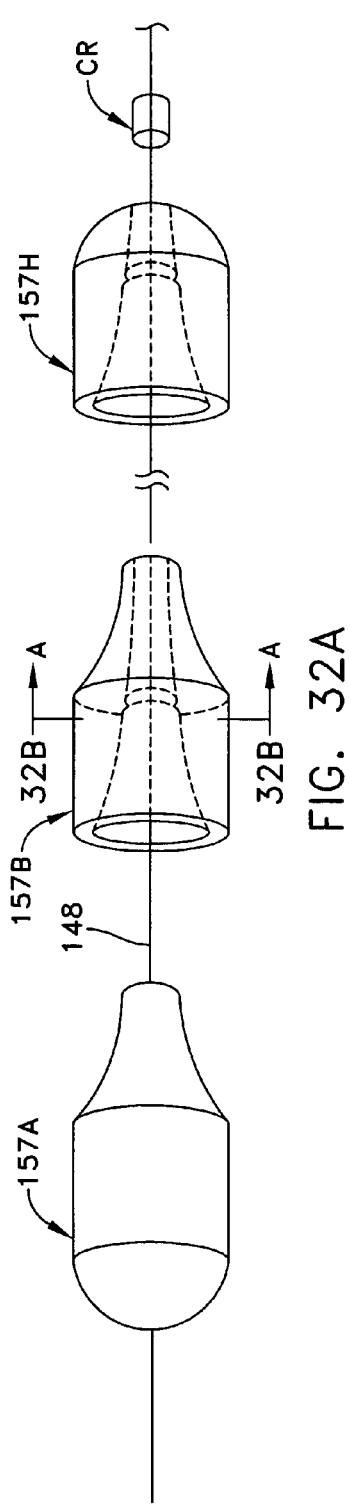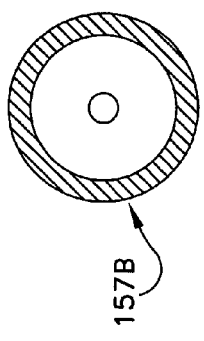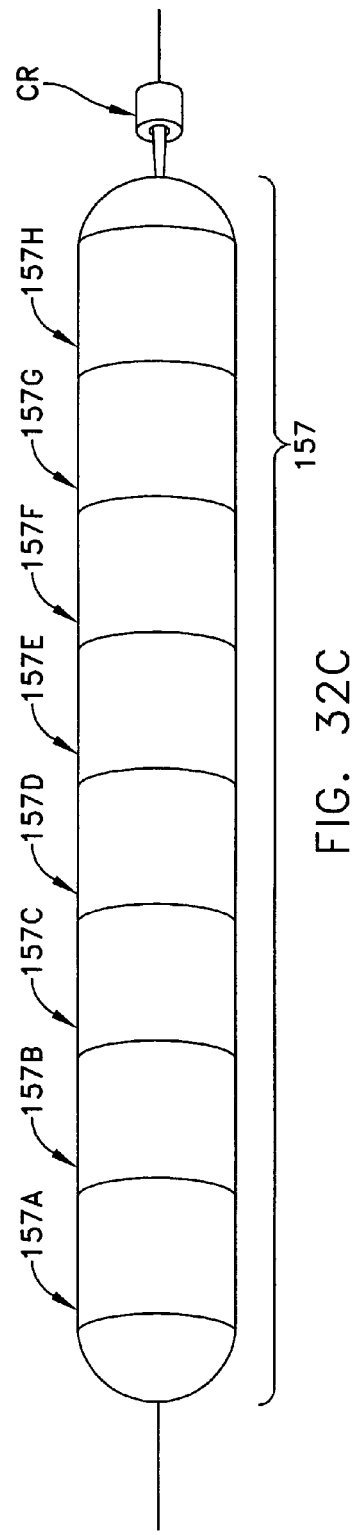
FIG. 32A
FIG. 32B
FIG. 32C

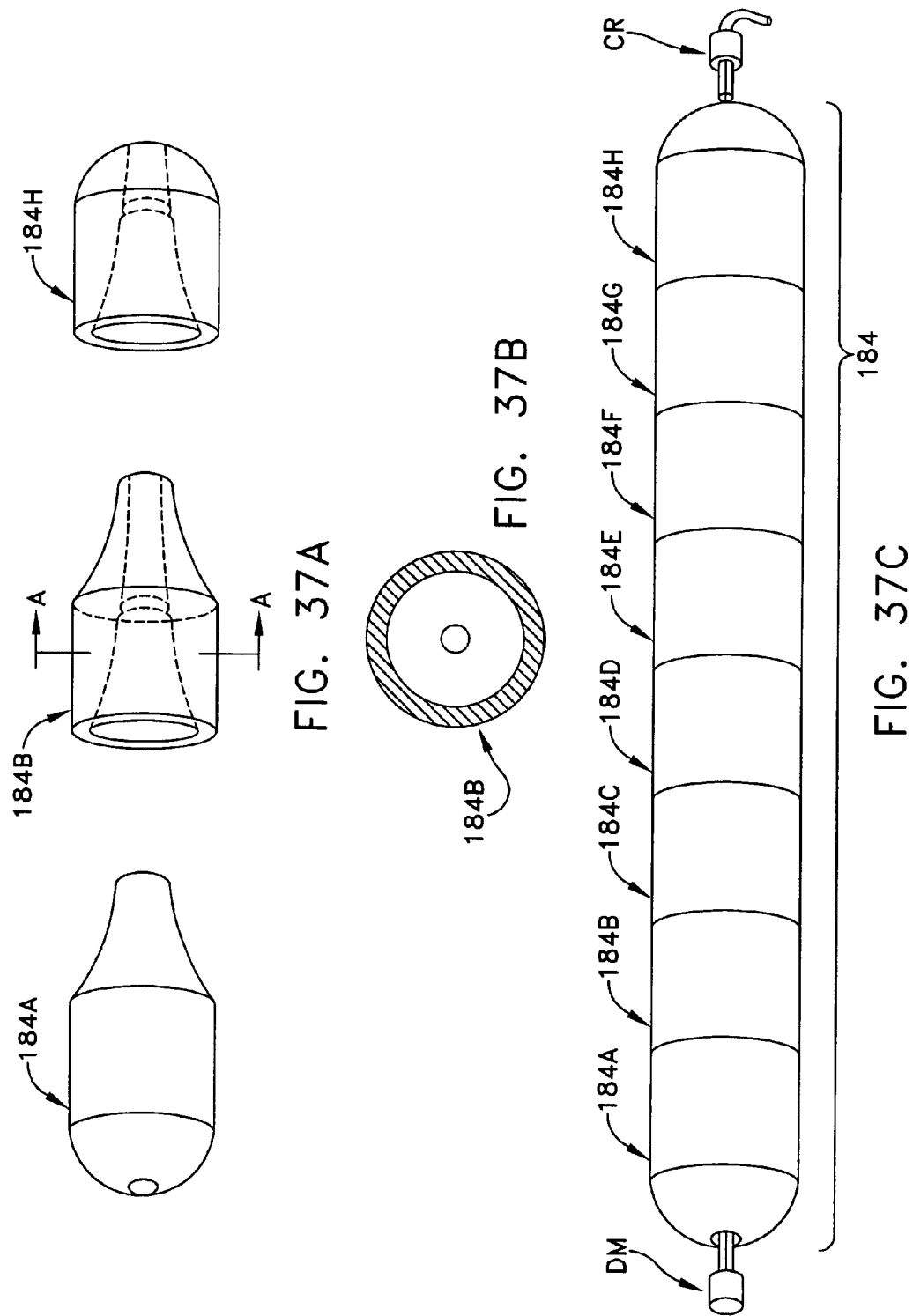

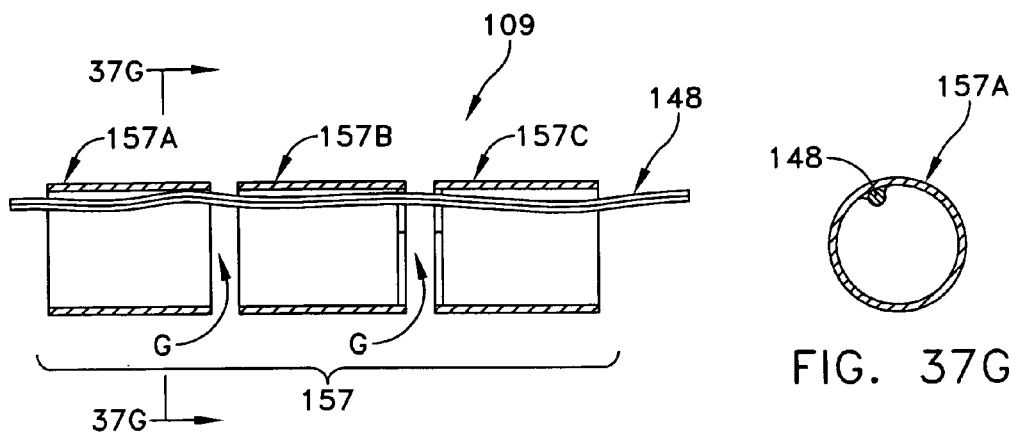
FIG. 37F
FIG. 37G
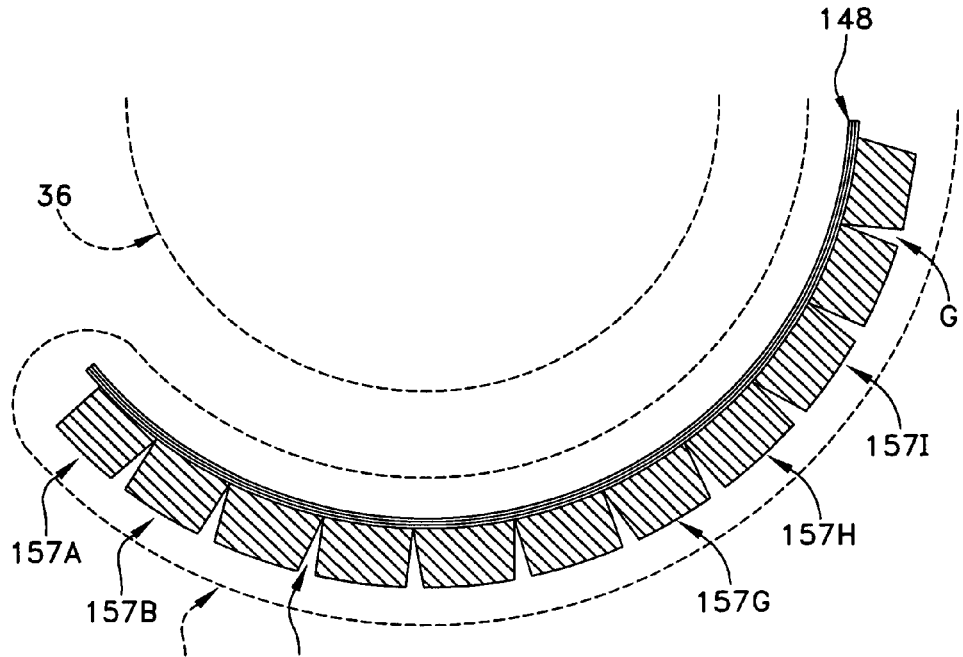
FIG. 37H
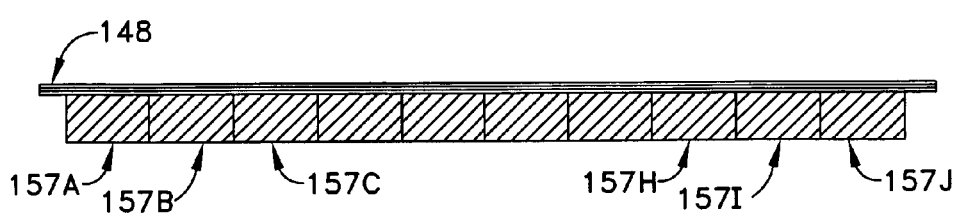
FIG. 37I

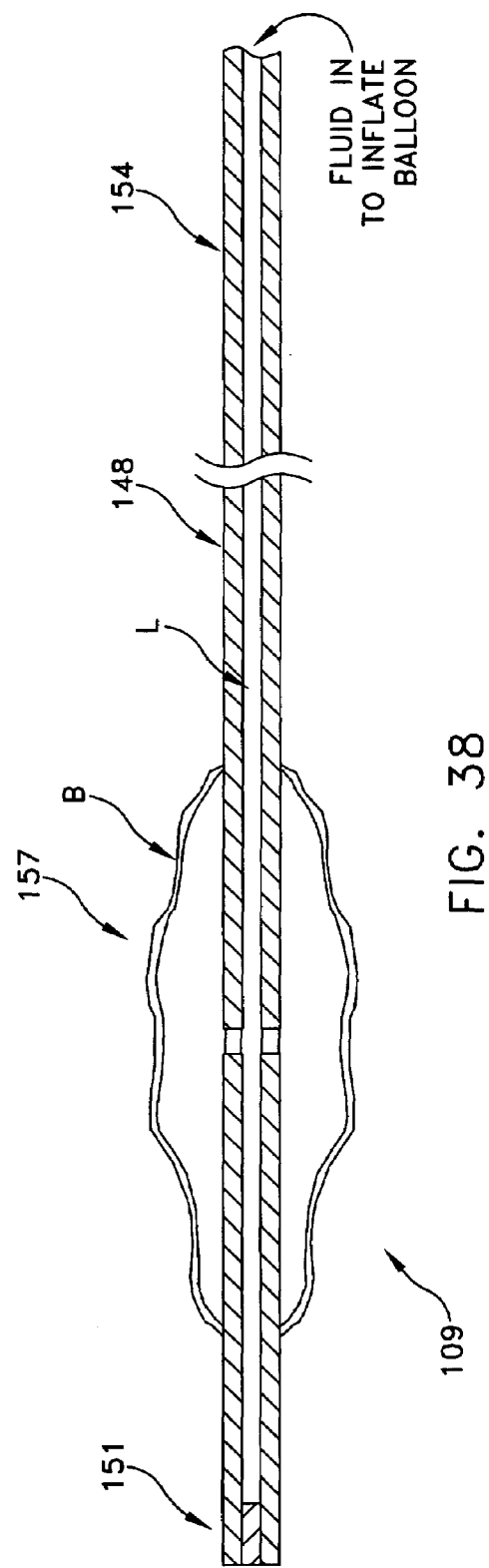

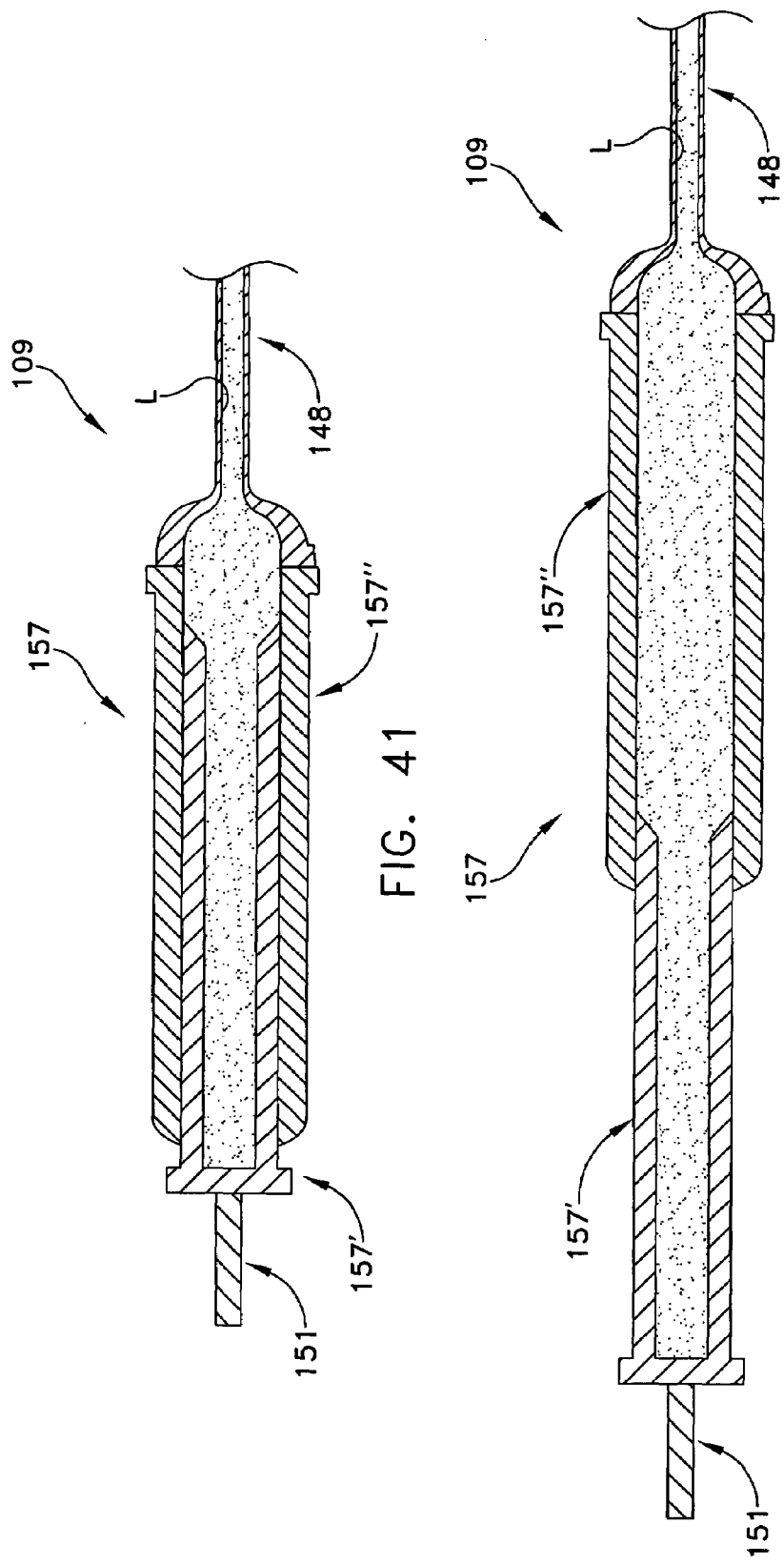

METHOD AND APPARATUS FOR IMPROVING MITRAL VALVE FUNCTION

REFERENCE TO PENDING PRIOR PATENT APPLICATIONS

This patent application:

(1) is a continuation-in-part of prior U.S. patent application Ser. No. 10/068,264, filed Feb. 5, 2002 now U.S. Pat. No. 6,656,221 by Daniel C. Taylor et al. for METHOD AND APPARATUS FOR IMPROVING MITRAL VALVE FUNCTION;

(2) claims benefit of pending prior U.S. Provisional Patent Application Ser. No. 60/279,974, filed Mar. 29, 2001 by Daniel C. Taylor et al. for METHOD AND APPARATUS TO IMPROVE MITRAL VALVE FUNCTION.

(3) claims benefit of pending prior U.S. Provisional Patent Application Ser. No. 60/280,038, filed Mar. 30, 2001 by William E. Cohn et al. for METHODS AND APPARATUS FOR TEMPORARY IMPROVEMENT IN MITRAL VALVE FUNCTION;

(4) claims benefit of pending prior U.S. Provisional Patent Application Ser. No. 60/279,973, filed Mar. 29, 2001 by Daniel C. Taylor et al. for METHODS AND DEVICES TO IMPROVE MITRAL VALVE FUNCTION;

(5) claims benefit of pending prior U.S. Provisional Patent Application Serial No. 60/283,820, filed Apr. 13, 2001 by William E. Cohn et al. for METHOD AND APPARATUS FOR TEMPORARY IMPROVEMENT IN MITRAL VALVE FUNCTION;

(6) claims benefit of pending prior U.S. Provisional Patent Application Ser. No. 60/312,217, filed Aug. 14, 2001 by Daniel C. Taylor et al. for METHOD AND APPARATUS FOR TEMPORARY IMPROVEMENT IN MITRAL VALVE FUNCTION;

(7) claims benefit of pending prior U.S. Provisional Patent Application Ser. No. 60/339,481, filed Oct. 26, 2001 by William E. Cohn et al. for TRANSVASCULAR APPROACH TO MITRAL VALVE PROCEDURES; and (8) claims benefit of pending prior U.S. Provisional Patent Application Ser. No. 60/348,424, filed Jan. 14, 2002 by Daniel C. Taylor et al. for METHOD AND APPARATUS TO IMPROVE MITRAL VALVE FUNCTION.

The aforementioned eight (8) patent applications are hereby incorporated herein by reference.

FIELD OF THE INVENTION

This invention relates to surgical methods and apparatus in general, and more particularly to surgical methods and apparatus for improving mitral valve function.

BACKGROUND OF THE INVENTION

Mitral valve repair is the procedure of choice to correct mitral regurgitation of all etiologies. With the use of current surgical techniques, between 70% and 95% of regurgitant mitral valves can be repaired. The advantages of mitral valve repair over mitral valve replacement are well documented. These include better preservation of cardiac function and reduced risk of anticoagulant-related hemorrhage, thromboembolism and endocarditis.

In current practice, mitral valve surgery requires an extremely invasive approach that includes a chest wall incision, cardiopulmonary bypass, cardiac and pulmonary arrest, and an incision on the heart itself to gain access to the mitral valve. Such a procedure is associated with high morbidity and mortality. Due to the risks associated with this procedure, many of the sickest patients are denied the potential benefits of surgical correction of mitral regurgitation. In addition, patients with moderate, symptomatic mitral regurgitation are denied early intervention and undergo surgical correction only after the development of cardiac dysfunction.

Mitral regurgitation is a common occurrence in patients with heart failure and a source of important morbidity and mortality in these patients. Mitral regurgitation in patients with heart failure is caused by changes in the geometric configurations of the left ventricle, papillary muscles and mitral annulus. These geometric alterations result in incomplete coaptation of the mitral leaflets during systole. In this situation, mitral regurgitation is corrected by plicating the mitral valve annulus, either by sutures alone or by sutures in combination with a support ring, so as to reduce the circumference of the distended annulus and restore the original geometry of the mitral valve annulus.

More particularly, current surgical practice for mitral valve repair generally requires that the mitral valve annulus be reduced in radius by surgically opening the left atrium and then fixing sutures, or more commonly sutures in combination with a support ring, to the internal surface of the annulus; this structure is used to pull the annulus back into a smaller radius, thereby reducing mitral regurgitation by improving leaflet coaptation.

This method of mitral valve repair, generally termed "annuloplasty", effectively reduces mitral regurgitation in heart failure patients. This, in turn, reduces symptoms of heart failure, improves quality of life and increases longetivity. Unfortunately, however, the invasive nature of mitral valve surgery and the attendant risks render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for medical, interventional or surgical therapy.

SUMMARY OF THE INVENTION

As a result, one object of the present invention is to provide an improved method and apparatus for reducing mitral regurgitation.

Another object of the present invention is to provide a method and apparatus for reducing mitral regurgitation which is minimally invasive.

Another object of the present invention is to provide a method and apparatus for reducing mitral regurgitation which can be deployed either permanently (e.g., for patients suffering from heart failure) or temporarily (e.g., for patients suffering front mitral regurgitation with acute myocardial infarction).

These and other objects are addressed by the present invention, which comprises an improved method and apparatus for reducing mitral regurgitation.

In one form of the invention, there is provided a method for reducing mitral regurgitation comprising: inserting apparatus into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising: inserting apparatus into the coronary sinus of a patient in the vicinity of the posterior leaflet of the mitral valve, the apparatus being adapted to move at least a portion of the coronary sinus in the vicinity of the posterior leaflet of the mitral valve anteriorly, whereby to move the posterior annulus anteriorly and thereby improve leaflet coaptation.

In another form of the invention, there is provided a method for reducing mitral regurgitation comprising: inserting apparatus into the coronary sinus of a patient in the vicinity of the posterior leaflet of the mitral valve, the apparatus being adapted to reduce the degree of natural curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising: inserting apparatus into the coronary sinus of a patient in the vicinity of the posterior leaflet of the mitral valve, the apparatus being adapted to increase the natural radius of curvature of at least a portion of the coronary sinus in the vicinity of the posterior leaflet of the mitral valve, whereby to move the posterior annulus anteriorly and thereby improve leaflet coaptation.

In another form of the invention, there is provided a method for reducing mitral regurgitation comprising: inserting apparatus into the coronary sinus of a patient in the vicinity of the posterior leaflet of the mitral valve, the apparatus having a distal end, a proximal end and an intermediate portion, the apparatus being configured so that when the apparatus is positioned in the coronary sinus in the vicinity of the posterior leaflet of the mitral valve, the distal and proximal ends will apply a posteriorly-directed force to the walls of the coronary sinus and the intermediate portion will apply an anteriorly-directed force to the walls of the coronary sinus, whereby to move the posterior annulus anteriorly and thereby improve leaflet coaptation.

In another form of the invention, there is provided a method for reducing mitral regurgitation comprising: inserting a substantially straight elongated body into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation.

In another form of the invention, there is provided a method for reducing mitral regurgitation comprising: inserting a substantially rigid elongated body into the coronary sinus of a patient in the vicinity of the posterior leaflet of the mitral valve, the substantially rigid elongated body being configured relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation.

In another form of the invention, there is provided a method for reducing mitral regurgitation comprising: inserting a straight, substantially rigid elongated body into the coronary sinus of a patient in the vicinity of the posterior leaflet of the mitral valve, the length of the straight, substantially rigid elongated body being sized relative to the natural curvature of the coronary sinus in the vicinity of the posterior leaflet of the mitral valve so that when the straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus and thereby improve leaflet coaptation.

In another form of the invention, there is provided an apparatus for reducing mitral regurgitation comprising: a body having a distal end, a proximal end and an intermediate portion, the body being configured so that when the body is positioned in the coronary sinus in the vicinity of the posterior leaflet of the mitral valve, the distal and proximal ends will apply a posteriorly-directed force to the walls of the coronary sinus, and the intermediate portion will apply an anteriorly-directed force to the walls of the coronary sinus, whereby to move the posterior annulus of the mitral valve anteriorly and thereby improve leaflet coaptation.

In another form of the invention, there is provided an apparatus for reducing mitral regurgitation comprising: a substantially straight elongated body adapted to be inserted into the coronary sinus of a patient in the vicinity of the posterior leaflet of the mitral valve, the length of the substantially straight elongated body being sized relative to the natural curvature of the coronary sinus in the vicinity of the posterior leaflet of the mitral valve so that when the substantially straight elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

In another form of the invention, there is provided an apparatus for reducing mitral regurgitation comprising: a substantially rigid elongated body adapted to be inserted into the coronary sinus of a patient in the vicinity of the posterior leaflet of the mitral valve, the length of the straight, substantially rigid elongated body being sized relative to the natural curvature of the coronary sinus in the vicinity of the posterior leaflet of the mitral valve so that when the substantially rigid elongated body is positioned in the coronary sinus, it will cause at least a portion of the coronary sinus to assume a different configuration adjacent to the posterior leaflet of the mitral valve, whereby to move the posterior annulus anteriorly and thereby improve leaflet coaptation.

In another form of the invention, there is provided an apparatus for reducing mitral regurgitation comprising: a straight, substantially rigid elongated body adapted to be inserted into the coronary sinus of a patient in the vicinity of the posterior leaflet of the mitral valve, the length of the straight, substantially rigid elongated body being sized relative to the natural curvature of the coronary sinus in the vicinity of the posterior leaflet of the mitral valve so that when the straight, substantially rigid elongated body is positioned in the coronary sinus, it will cause at least a portion of the coronary sinus to assume a substantially straight configuration adjacent to the posterior leaflet of the mitral valve, whereby to increase the radius of curvature of the mitral annulus, moving it anteriorly, and thereby improve leaflet coaptation.

Significantly, the present invention may be practiced in a minimally invasive manner, either permanently or temporarily, so as to reduce mitral regurgitation.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 10 and 11 show alternative constructions for the straight, substantially rigid elongated body;

FIGS. 25–27 illustrate another form of the present invention;

FIGS. 32A–32C illustrate another aspect of the present invention;

FIGS. 37A–37C illustrate another aspect of the present invention;

FIGS. 37F–37I illustrate another aspect of the present invention;

FIG. 38 illustrates another form of the present invention;

FIGS. 41 and 42 illustrate yet another form of the present invention; and

DETAILED DESCRIPTION OF THE PREFERRED EMBODIMENTS

Figure 1:
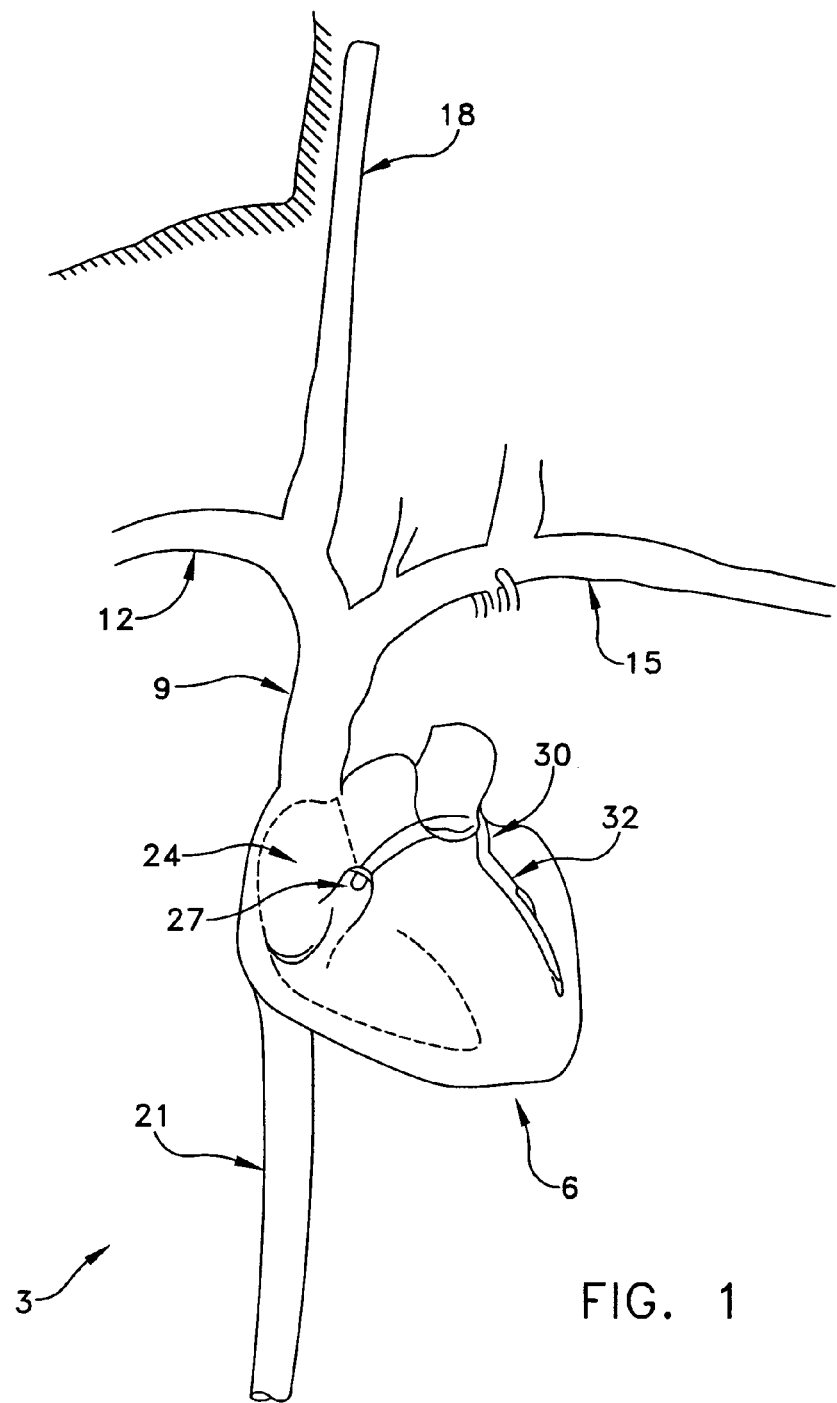
FIG. 1 is a schematic view of portions of the human vascular system.

The coronary sinus is the largest vein in the human heart. During a large portion of its course in the atrioventricular groove, the coronary sinus typically extends adjacent to the left atrium of the heart for a distance of approximately 5 to 10 centimeters. Significantly, for a portion of its length, e.g., typically approximately 7–9 cm, the coronary sinus extends substantially adjacent to the posterior perimeter of the mitral annulus. The present invention takes advantage of this consistent anatomic relationship. More particularly, by deploying novel apparatus in the coronary sinus, adjacent to the posterior leaflet of the mitral valve, the natural curvature of the coronary sinus may be modified in the vicinity of the posterior leaflet of the mitral valve, whereby to move the posterior annulus anteriorly so as to improve leaflet coaptation and, as a result, reduce mitral regurgitation.

In one preferred embodiment of the invention, the novel apparatus comprises a straight, substantially rigid elongated body, the length of the straight, substantially rigid elongated body being sized so that when the straight, substantially rigid body is positioned in the coronary sinus in the vicinity of the posterior leaflet of the mitral valve, the straight, substantially rigid elongated body will cause at least a portion of the coronary sinus to assume a substantially straight configuration adjacent to the posterior leaflet of the mitral valve, whereby to move the posterior annulus anteriorly and thereby improve leaflet coaptation.

And in one preferred embodiment of the invention, access to the coronary sinus is gained percutaneously, e.g., the straight, substantially rigid elongated body is introduced into the patient's vascular system via the jugular vein or via the left subclavian vein, passed down the superior vena cava, passed through the right atrium and then passed into the coronary sinus, where it is deployed. Alternatively, the straight, substantially rigid elongated body may be introduced into the coronary sinus through a small incision in the heart, or through some other incision into the patient's vascular system.

And in one preferred embodiment of the invention, the straight, substantially rigid elongated body is guided into position by (i) passing it through a pre-positioned catheter, or (ii) passing it over a pre-positioned guidewire, or (iii) passing it guide-free (e.g., on the end of a steerable delivery tool) to the surgical site.

Once deployed, the novel apparatus may be left in position permanently (e.g., in the case of patients suffering from mitral regurgitation associated with heart failure) or the novel apparatus may be left in position only temporarily (e.g., in the case of patients suffering from mitral regurgitation associated with acute myocardial infarction).

Visualization of the procedure may be obtained by fluoroscopy, echocardiography, intravascular ultrasound, angioscopy, real-time magnetic resonance imaging, etc. The efficacy of the procedure may be determined through echocardiography, although other imaging modalities may also be suitable.

Figure 2:
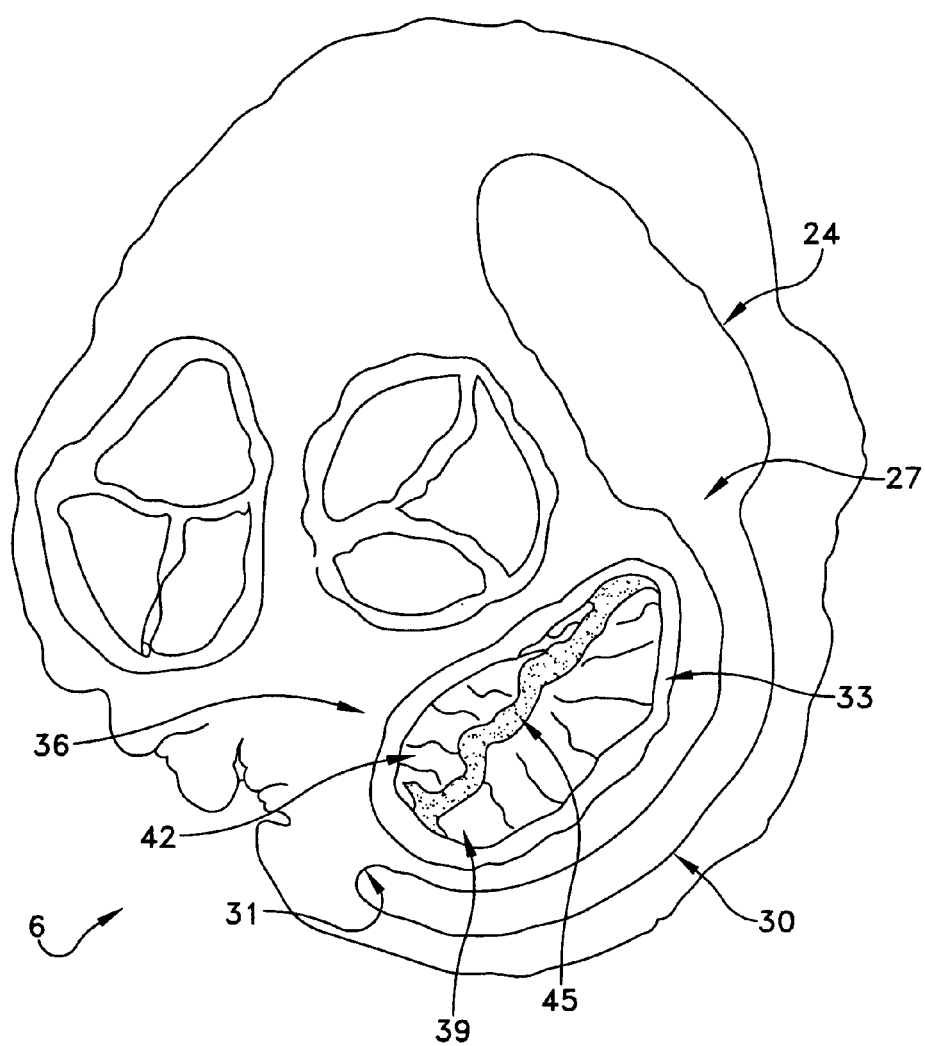
FIG. 2 is a schematic view of portions of the human heart.

Looking now at FIGS. 1 and 2, there are shown aspects of the cardiovascular system 3 of a patient. More particularly, cardiovascular system 3 generally comprises the heart 6, the superior vena cava 9 (FIG. 1), the right subclavian vein 12, the left subclavian vein 15, the jugular vein 18, and the inferior vena cava 21. Superior vena cava 9 and inferior vena cava 21 communicate with the heart's right atrium 24 (FIGS. 1 and 2). The coronary ostium 27 leads to coronary sinus 30. At the far end 31 (FIG. 2) of coronary sinus 30, the vascular structure turns into the vertically-descending anterior interventricular vein ("AIV") 32 (FIG. 1). For purposes of the present invention, it can generally be convenient to consider the term "coronary sinus" to mean the vascular structure extending between coronary ostium 27 and AIV 32.

As seen in FIG. 2, between coronary ostium 27 and AIV 32, coronary sinus 30 generally extends substantially adjacent to the posterior perimeter of the annulus 33 of the mitral valve 36. Mitral valve 36 comprises a posterior leaflet 39 and an anterior leaflet 42. In the case of a regurgitant mitral valve, posterior leaflet 39 and anterior leaflet 42 will generally fail to properly coapt at systole, thereby leaving an intervening gap 45 which will permit regurgitation.

Figure 3:
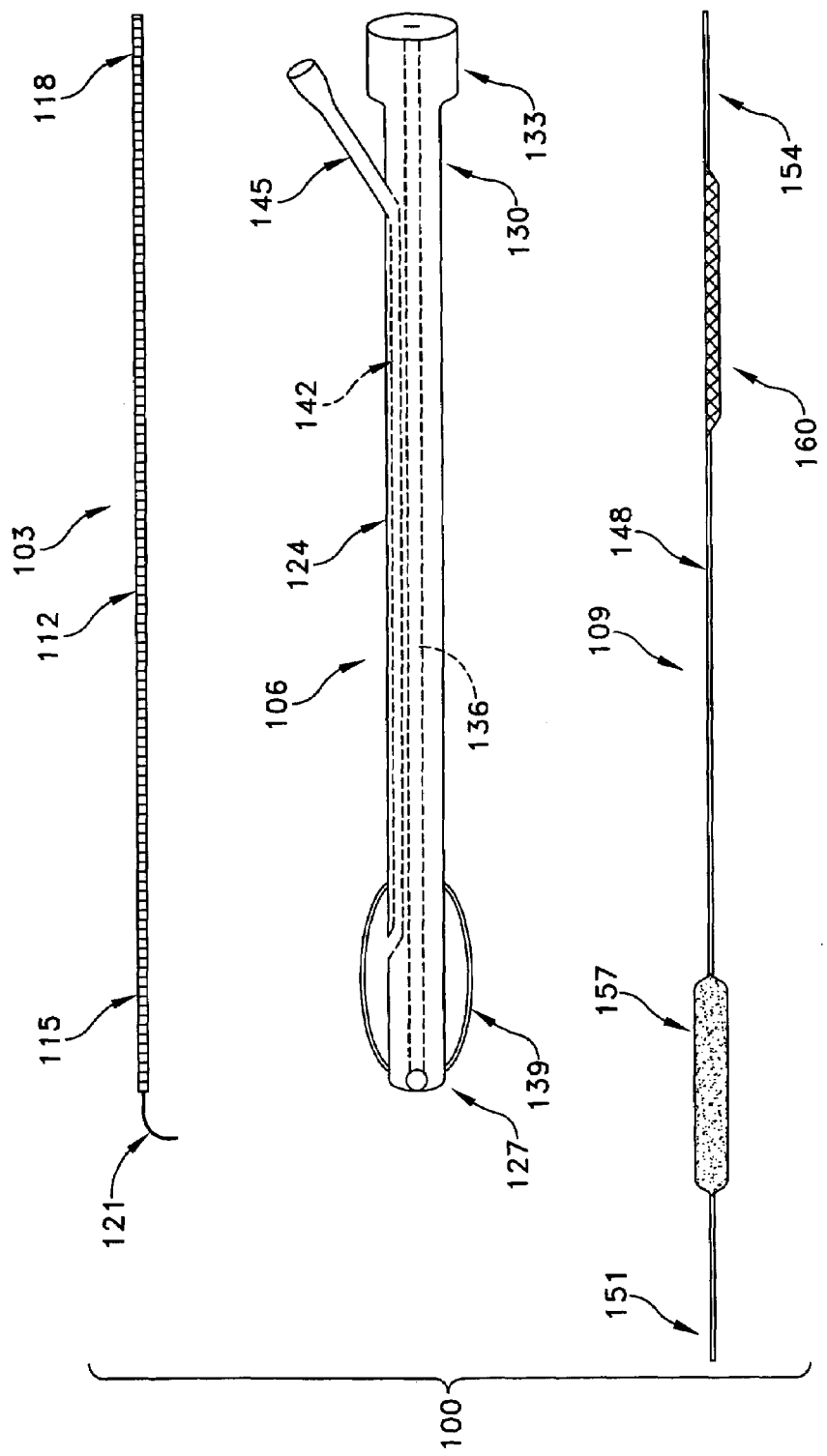
FIG. 3 is a schematic view of a preferred system formed in accordance with the present invention.

Looking next at FIG. 3, there is shown a system 100 which comprises one preferred embodiment of the present invention. More particularly, system 100 generally comprises a guidewire 103, a delivery catheter 106 and a push rod 109.

Guidewire 103 comprises a flexible body 112 having a distal end 115 and a proximal end 118. The distal end 115 of guidewire 103 preferably includes a spring tip 121 for allowing the distal end of guidewire 103 to atraumatically traverse vascular structures, i.e., while the guidewire is being passed through the vascular system of a patient.

Delivery catheter 106 comprises a flexible body 124 having a distal end 127 and a proximal end 130, preferably with an adjustable valve 133 attached. A central lumen 136 extends from distal end 127 to proximal end 130. In some circumstances it may be desirable to provide a securing mechanism for securing the distal end of the delivery catheter within a vascular structure. By way of example but not limitation, a balloon 139 may be positioned about the exterior of flexible body 124, just proximal to distal end 127, with an inflation lumen 142 extending between balloon 139 and an inflation fitting 145.

Push rod 109 comprises a flexible body 148 having a distal end 151 and a proximal end 154. A straight, substantially rigid elongated body 157, which may have a variety of different lengths, is formed on flexible body 148, proximal to distal end 151. A removable proximal stiffener or handle 160 may be placed between straight, substantially rigid elongated body 157 and proximal end 154.

System 100 may be used as follows to reduce mitral regurgitation.

First, distal end 115 of guidewire 103 is passed down the jugular vein 18 (or the left subclavian vein 15) of a patient, down superior vena cava 9, through right atrium 24 of the heart, and then into coronary sinus 30. See FIG. 4. It will be appreciated that as flexible guidewire 103 is passed down coronary sinus 30, the guidewire will tend to assume the natural curved shape of the coronary sinus, due to the flexible nature of the guidewire. The guidewire's atraumatic spring tip 121 will help ensure minimal damage to vascular structures as guidewire 103 is maneuvered into position.

Next, distal end 127 of delivery catheter 106 is placed over proximal end 118 of guidewire 103 and passed down the guidewire until the distal end of the delivery catheter is positioned in coronary sinus 30. See FIG. 5. Again, it will be appreciated that as the flexible delivery catheter 106 passes down the coronary sinus, the delivery catheter will tend to assume the natural curved shape of the coronary sinus, due to the flexible nature of the delivery catheter.

Once delivery catheter 106 has been positioned within the coronary sinus, guidewire 103 is removed. See FIG. 6. Either before or after guidewire 103 is removed, balloon 139 may be inflated so as to secure distal end 127 of delivery catheter 106 in position within coronary sinus 30.

Next, push rod 109 is passed down the central lumen 136 of delivery catheter 106. As the push rod's straight, substantially rigid elongated body 157 is passed down central lumen 136 of delivery catheter 106, it will force the delivery catheter to assume a straight configuration at the point where the straight, substantially rigid elongated body 157 currently resides. As push rod 109 is pushed down delivery catheter 106, balloon 139 will hold the distal end of the delivery catheter in position within coronary sinus 30.

Push rod 109 is pushed down delivery catheter 106, utilizing removable proximal stiffener 160 as needed, until the straight, substantially rigid elongated body 157 is located adjacent to the posterior annulus of mitral valve 36. See FIG. 7. As this occurs, the presence of the straight, substantially rigid elongated body 157 in delivery catheter 106 will cause at least a portion of coronary sinus 30 to assume a substantially straight configuration at this point, so that the posterior annulus of mitral valve 36 is forced anteriorly. This will cause the mitral valve's posterior leaflet 39 to also move anteriorly so as to improve mitral valve leaflet coaptation and thereby reduce (or completely eliminate) mitral valve regurgitation. In this respect it should be appreciated that the posterior annulus may be shifted anteriorly so as to achieve, or to attempt to achieve to the extent anatomically possible, leaflet-to-leaflet engagement or leaflet-to-annulus engagement (e.g., where a leaflet may be tethered due to left ventricular distortion). Both of these types of engagement, or targeted engagement, are intended to be encompassed by the terms "improved leaflet coaptation" and/or "increased leaflet coaptation" and the like. Using standard visualization means (e.g. echocardiography or fluoroscopy), the exact position of the straight, substantially rigid elongated body 157 is adjusted so as to reduce (or completely eliminate) regurgitation in mitral valve 36.

In this respect it should be appreciated that the straight, substantially rigid elongated body 157 is preferably sized to be somewhat less than the length of the coronary sinus between coronary ostium 27 and AIV 32. However, in some circumstances it may be desirable to size the straight, substantially rigid elongated body 157 so that it will extend out of the coronary sinus and into the right atrium.

Furthermore, it should also be appreciated that the system provides a degree of tactile feedback to the user during deployment. More particularly, substantial resistance will typically be encountered as the straight, substantially rigid elongated body 157 is pushed out of right atrium 24 and into coronary sinus 30; then resistance will typically drop as body 157 is moved through the coronary sinus; and then resistance will typically increase significantly again as the distal tip of body 157 comes to the far end 31 of the coronary sinus. Thus, there is a sort of tactile "sweet spot" when the straight, substantially rigid elongated body 157 is located in the coronary sinus between coronary ostium 27 and AIV 32, and this tactile "sweet spot" can be helpful to the user in positioning the straight, substantially rigid elongated body 157 in coronary sinus 30.

At this point the straight, substantially rigid elongated body 157 is locked in position, e.g., by closing adjustable valve 133, and balloon 139 may be deflated.

System 100 is left in this position until it is no longer needed. In some cases this may mean that system 100 is left in position for a period of a few hours, days or weeks; in other cases system 100 may be substantially permanent. If and when system 100 is to be removed, push rod 109 is removed from delivery catheter 106, and then delivery catheter 106 is removed from the patient.

Thus it will be seen that with the present invention, the straight, substantially rigid elongated body 157 is essentially force-fit into the normally curved portion of the coronary sinus adjacent to the mitral valve's posterior leaflet. By properly sizing the length of the straight, substantially rigid elongated body 157 relative to the natural curvature of the patient's anatomy, and by properly positioning the straight, substantially rigid elongated body 157 in the patient's coronary sinus, the straight, substantially rigid elongated body will cause at least a portion of the coronary sinus to assume a substantially straight configuration adjacent to the posterior leaflet of the mitral valve. This action will in turn drive the posterior annulus of the mitral valve anteriorly, so as to improve leaflet coaptation and thereby reduce mitral regurgitation. Thus, by inserting the straight, substantially rigid elongated body 157 into the coronary sinus adjacent to the posterior leaflet of the mitral valve, the annulus of the mitral valve is effectively manipulated so that it will assume an increased radius of curvature.

It has also been found that by inserting the straight, substantially rigid elongated body into the coronary sinus adjacent to the posterior leaflet of the mitral valve, the left ventricle may also be remodeled so as to help alleviate congestive heart failure.

Figure 7:
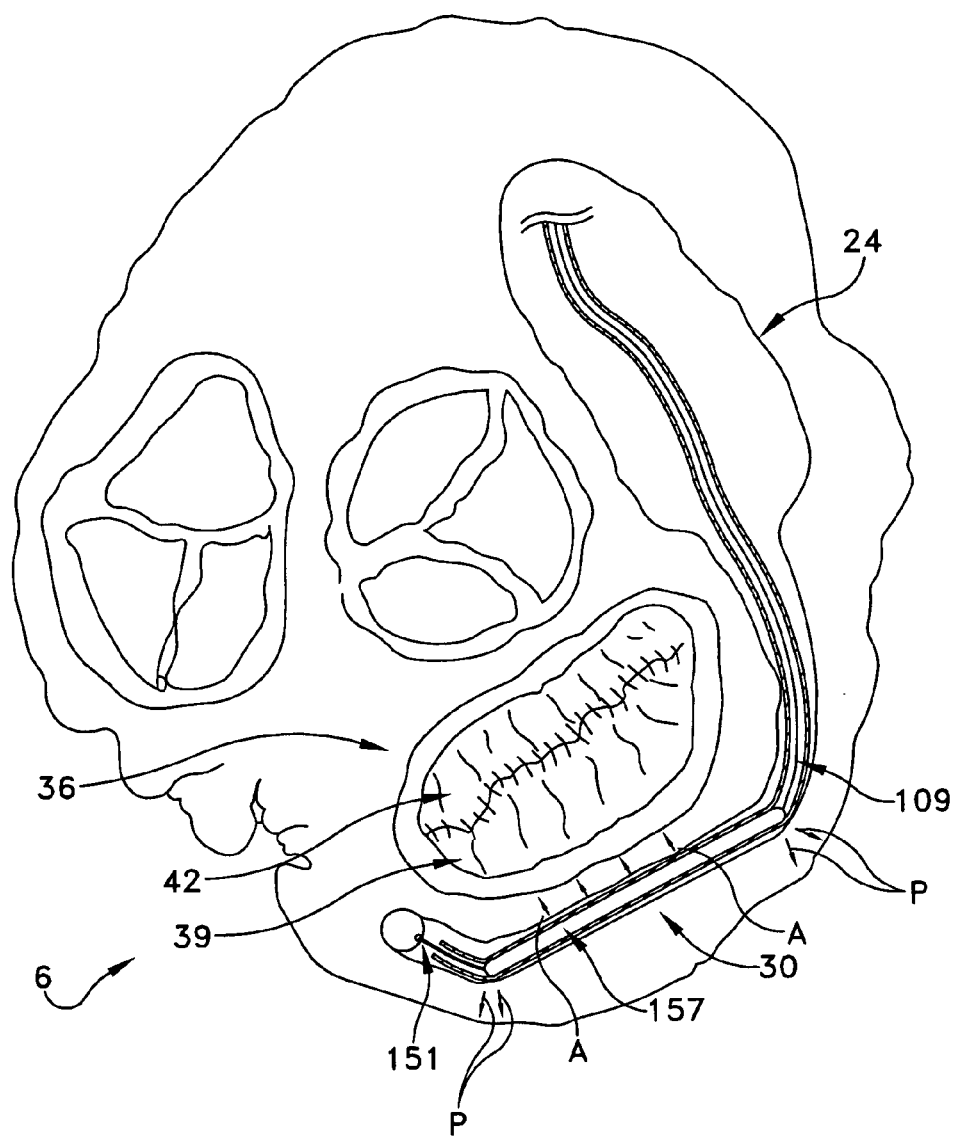

It is significant to note that with the present invention, the distal and proximal ends of straight, substantially rigid elongated body 157 apply a posteriorly-directed force on the walls of coronary sinus 30 (e.g., as shown with arrows P in FIG. 7) while the intermediate portion of straight, substantially rigid elongated body 157 applies an anteriorly-directed force on the walls of coronary sinus 30 (e.g., as shown with arrows A in FIG. 7).

Figure 8:
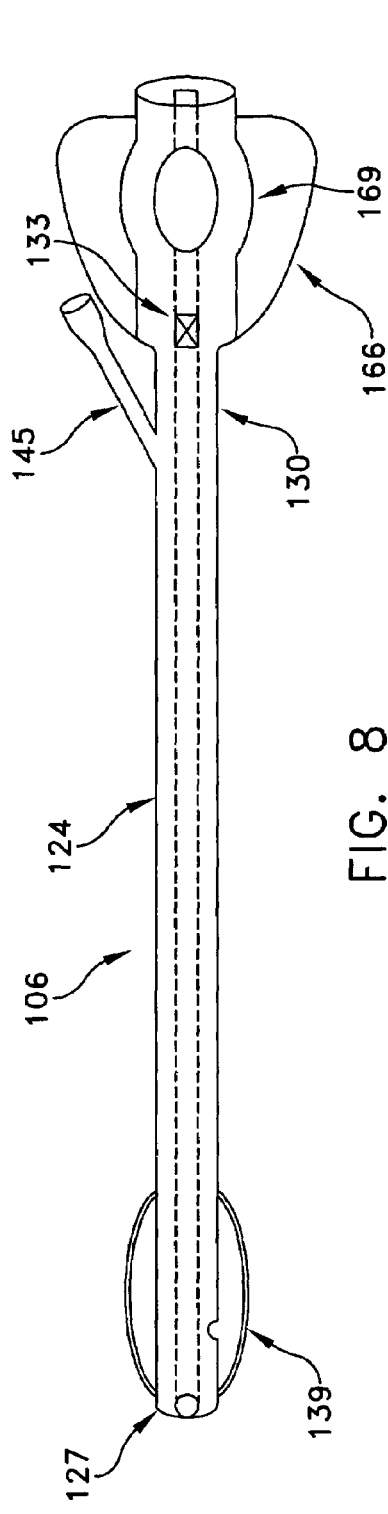
FIG. 8 shows an alternative form of delivery catheter.

In some cases the proximal end 130 of delivery catheter 106 may be fixed to the patient's outer skin using standard patient care methods such as adhesive tape, pursestring sutures, skin staples, etc. In other cases proximal end 130 of delivery catheter 106 may include a sewing cuff whereby the delivery catheter may be secured to the patient's tissue by suturing. See, for example, FIG. 8, where a sewing cuff 166 is shown attached to the proximal end 130 of delivery catheter 106. If desired, an element 169 may be provided proximal to adjustable valve 133, whereby flexible push rod 109 may be made fast to delivery catheter 106. By way of example, element 169 may comprise a crimpable element to secure flexible push rod 109 to delivery catheter 106, which is in turn secured to the patient. If desired, the proximal end of the assembly may be embedded under the skin of the patient, e.g., in the case of a permanent implant.

As noted above, it can be helpful to anchor the distal end of delivery catheter 106 in position within the coronary sinus prior to pushing push rod 109 into the delivery catheter. Such an arrangement will keep the delivery catheter in place as the push rod makes the turn within the right atrium and enters the coronary sinus. In the absence of such anchoring, the push rod may drive the delivery catheter down the inferior vena cava 21. By securing the distal end of delivery catheter 106 to the walls of coronary sinus 30, the delivery catheter can be stabilized against diversion down the inferior vena cava 21 when the straight, substantially rigid elongate body 157 encounters initial resistance to making the turn into the coronary sinus.

The balloon 139 is one way of accomplishing such anchoring. However, it is also possible to utilize other types of securing mechanisms to anchor the distal end 127 of delivery catheter 106 in position within coronary sinus 30, e.g., spring clips, ribs, etc.

Figure 9:
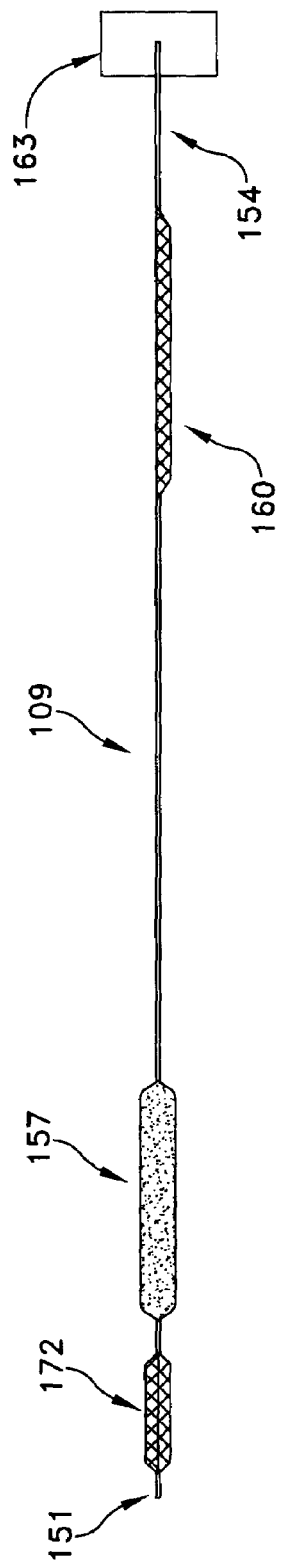
FIG. 9 shows an alternative form of flexible push rod.

Alternatively, and looking next at FIG. 9, the distal end 151 of push rod 109 may itself be provided with a distal anchor, e.g., such as the distal anchor 172 shown in FIG. 9.

Figure 9A:
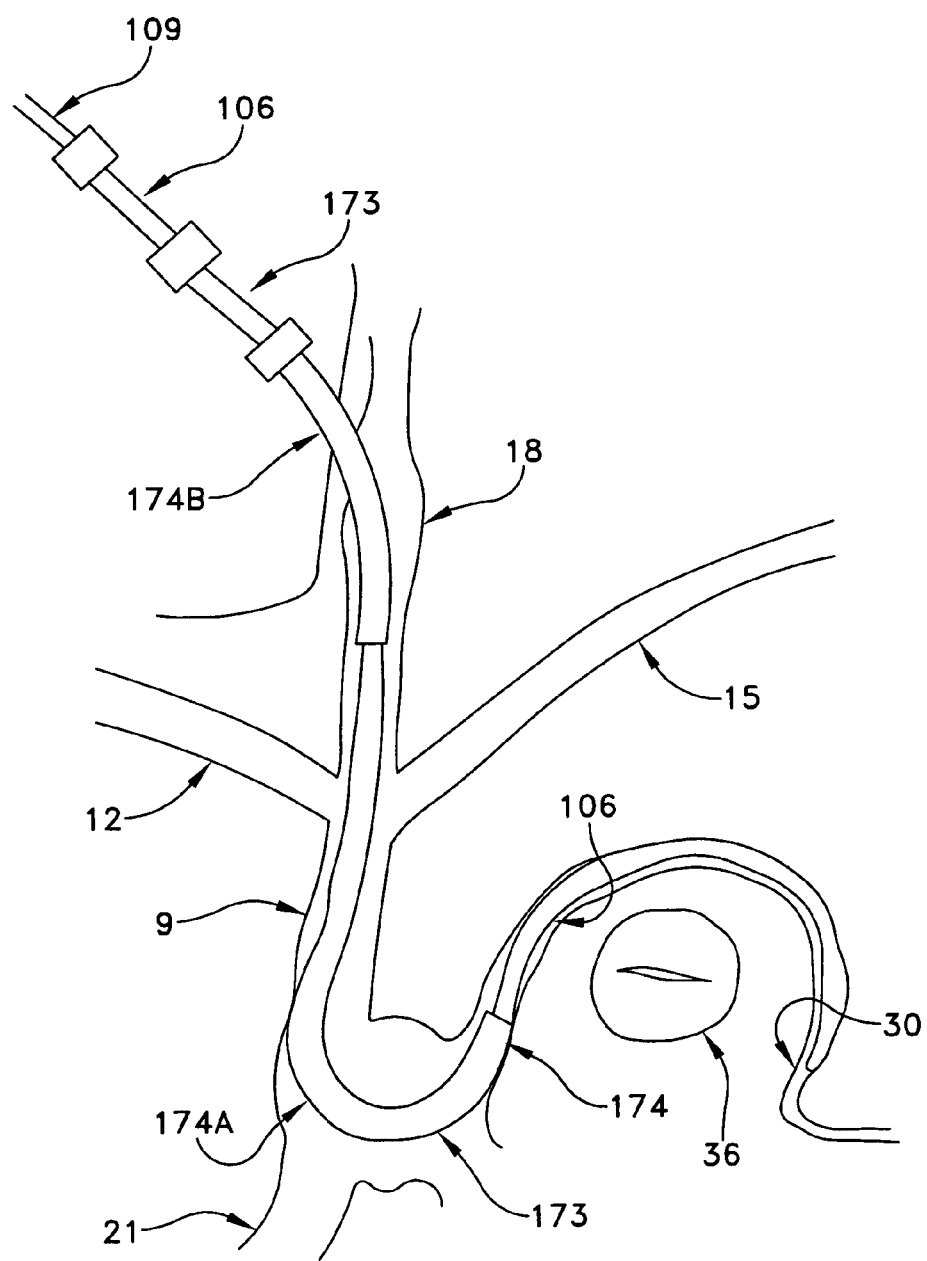
FIG. 9A shows another alternative form of the present invention.

It is also possible to prevent diversion of delivery catheter 106 down inferior vena cava 21 without anchoring the distal end of delivery catheter 106 or flexible push rod 109 to the walls of the coronary sinus. More particularly, and looking now at FIG. 9A, there is shown a support catheter 173 which is formed out of a more rigid material than delivery catheter 106. Support catheter 173 is constructed so that its distal end 174 can be positioned in coronary ostium 27 and then its sidewall 174A can support delivery catheter 106 adjacent to inferior vena cava 21 when push rod 109 is passed down delivery catheter 106, whereby to prevent delivery catheter 106 from diverting down inferior vena cava 21. FIG. 9A also shows an introducer catheter 174B at the entrance to jugular vein 18.

Figure 11A:
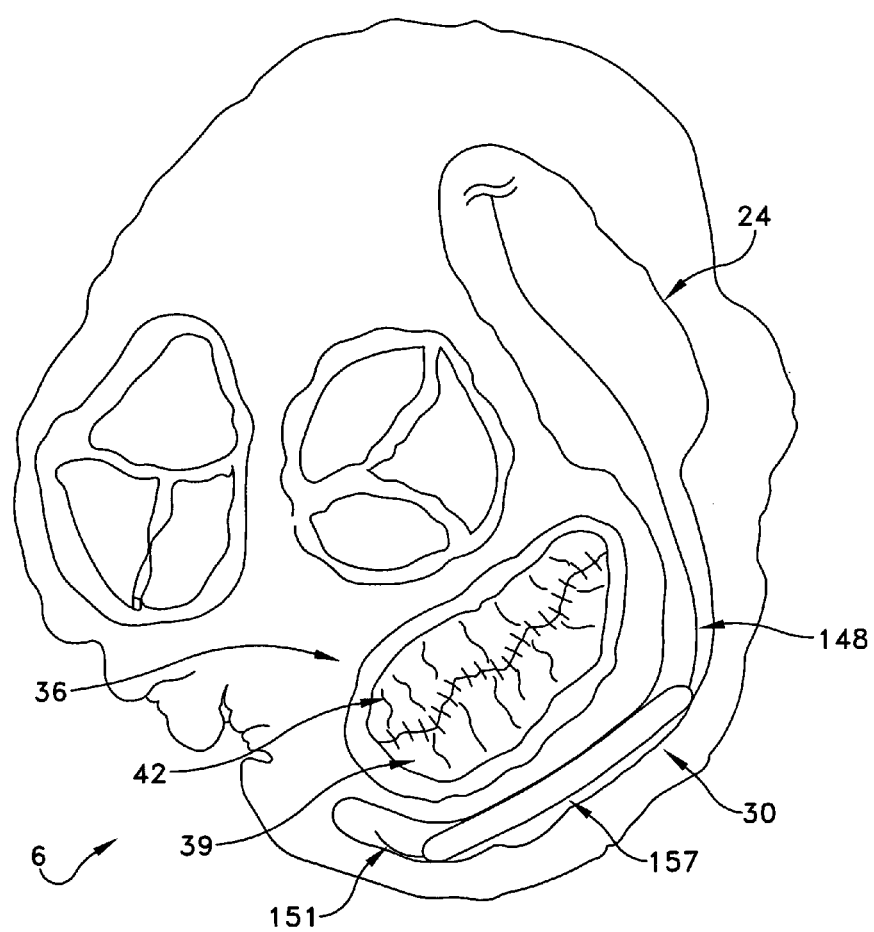
FIG. 11A illustrates another aspect of the present invention.

As noted above, as push rod 109 is advanced to the region adjacent to the posterior annulus of the mitral valve, the straight, substantially rigid elongated body 157 will distort the natural configuration of the coronary sinus so that it will assume a substantially straight configuration. While this action induces the desired valve remodeling, it can also induce a significant stress on the walls of the coronary sinus, particularly at the distal and proximal ends of the straight, substantially rigid elongated body 157, where stress will be concentrated. To this end, the construction of the straight, substantially rigid elongated body 157 may be modified somewhat so as to better distribute this stress. More particularly, and looking next at FIG. 10, the distal and proximal ends of straight, substantially rigid elongated body 157 may include relatively flexible portions 175 to help better distribute the stress exerted on the walls of the coronary sinus. Additionally, and/or alternatively, any taper applied to the distal and proximal ends of straight, substantially rigid elongated body 157 may be elongated, e.g., such as shown at 178 in FIG. 11, so as to better distribute the stress imposed on the walls of the coronary sinus.

In the preceding discussion of system 100, push rod 109 is described as being inserted to the surgical site through the delivery catheter 106 and remaining within delivery catheter 106 while at the surgical site and, when push rod 109 is to be removed, removing push rod 109 and then delivery catheter 106. However, if desired, once push rod 109 has been deployed at the surgical site, delivery catheter 106 may then be removed, leaving just push rod 109 at the surgical site. See, for example, FIG. 11A.

It is also possible to advance push rod 109 directly to the surgical site without passing it through a delivery catheter; in this case push rod 109 would be advanced on its own through the intervening vascular structure until it is deployed in coronary sinus 30.

Figure 12:
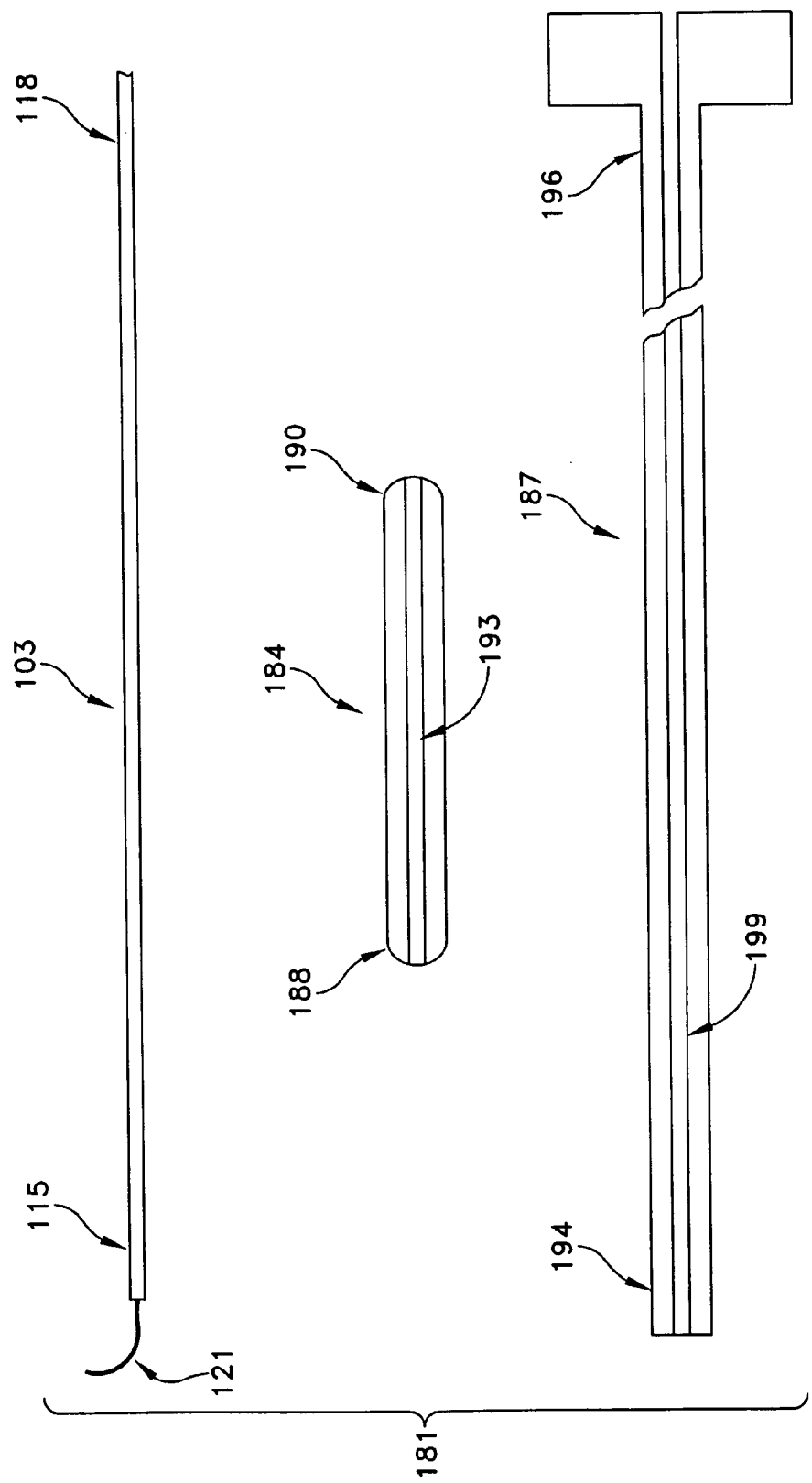
FIG. 12 shows an alternative system formed in accordance with the present invention.

Looking next at FIG. 12, there is shown a system 181 which comprises another preferred embodiment of the present invention. More particularly, system 181 generally comprises the guidewire 103, a straight, substantially rigid elongated body 184 and a push cannula 187.

Guidewire 103 is as previously described.

Straight, substantially rigid elongated body 184, which may have a variety of different lengths, comprises a distal end 188 and a proximal end 190. A central lumen 193 extends between distal end 188 and proximal end 190. Central lumen 193 accommodates guidewire 103.

Push cannula 187 comprises a distal end 194 and a proximal end 196. A central lumen 199 extends between distal end 194 and proximal end 196. Central lumen 199 accommodates guidewire 103.

Figure 13:
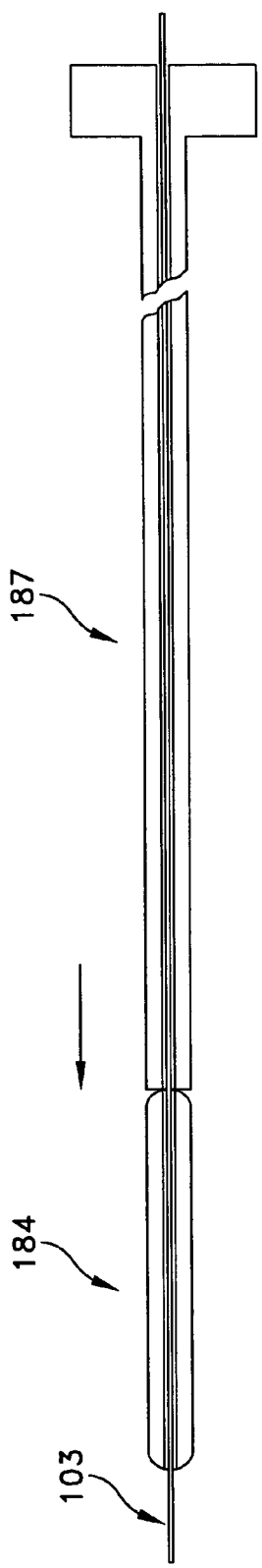
FIG. 13 shows use of the system shown in FIG. 12.

As a result of this construction, elongated body 184 and push cannula 187 may be mounted on guidewire 103, and push cannula 187 may be used to push elongated body 184 down guidewire 103. See FIG. 13.

System 181 may be used as follows to reduce mitral regurgitation.

Figure 14:
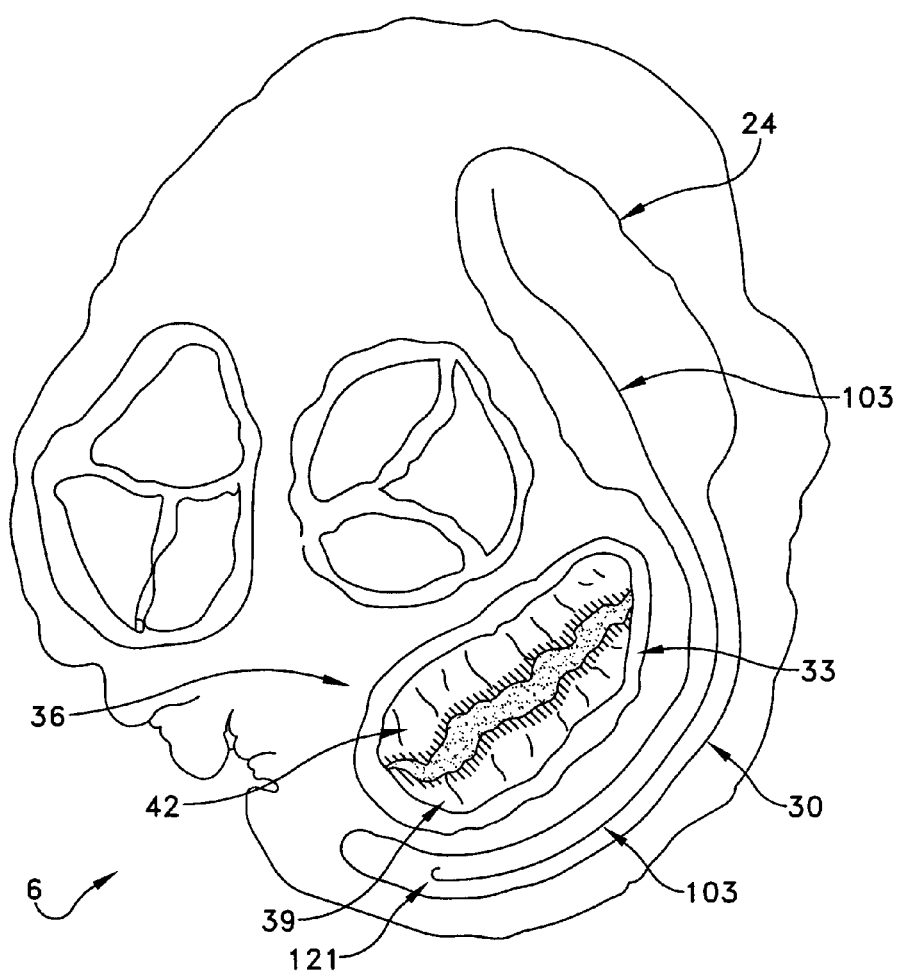
FIGS. 14–16 illustrate another aspect of the present invention.

First, distal end 115 of guidewire 103 is passed down jugular vein 18 (or the left subclavian vein 15) of a patient, down superior vena cava 9, through right atrium 24 of the heart, and into coronary sinus 30 (FIG. 14). It will be appreciated that as flexible guidewire 103 is passed down coronary sinus 30, the guidewire will tend to assume the natural curved shape of the coronary sinus, due to the flexible nature of the guidewire. The guidewire's atraumatic spring tip 121 will help minimize damage to vascular structures as the guidewire is advanced into position.

Figure 15:
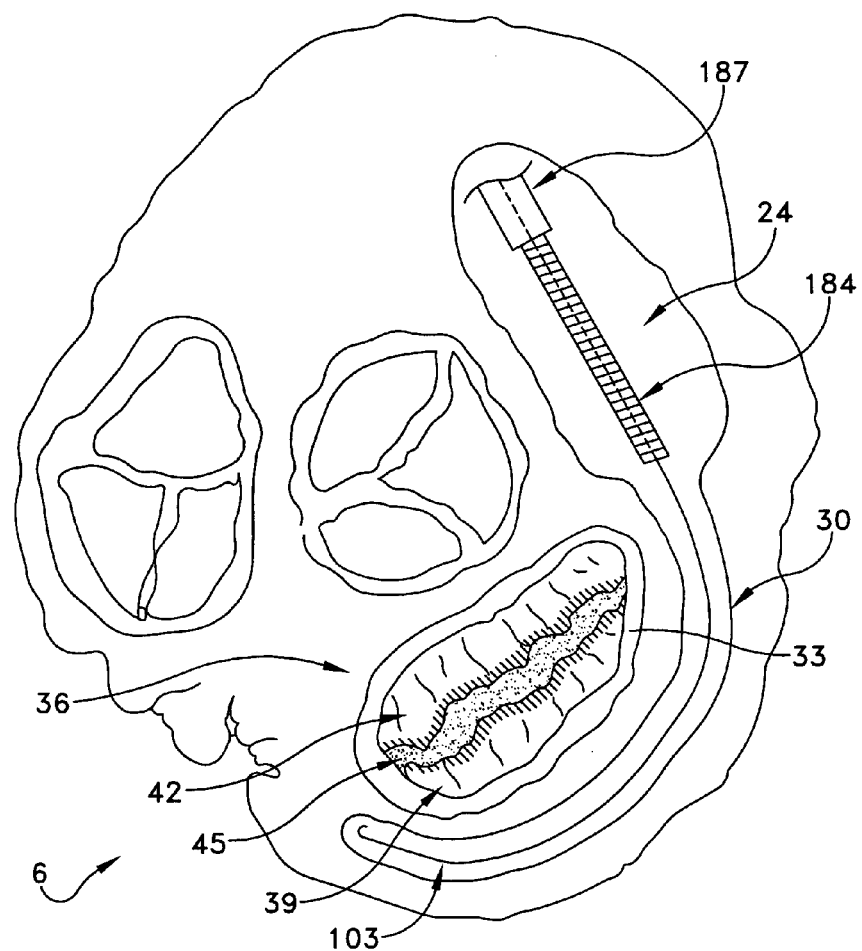

Next, distal end 188 of straight, substantially rigid elongated body 184 is placed over proximal end 118 of guidewire 103 and passed a short distance down the guidewire. Then the distal end 194 of push cannula 187 is placed over proximal end 118 of guidewire 103, and then push cannula 187 is advanced down the guidewire. As push cannula 187 is advanced down the guidewire, its distal end 194 pushes the straight, substantially rigid elongated body 184 ahead of it. See FIG. 15.

As the straight, substantially rigid elongated body 184 is passed down the coronary sinus, it will force the coronary sinus to assume a straight configuration at the point where the straight, substantially rigid elongated body 184 currently resides. Push cannula 187 is pushed down guidewire as needed, until the straight, substantially rigid elongated body 184 is located adjacent to the posterior annulus of the mitral valve. See FIG. 16. As this occurs, the presence of the straight, substantially rigid elongated body 184 in the coronary sinus will cause coronary sinus to assume a substantially straight configuration at this point, so that the posterior annulus of the mitral valve is forced anteriorly. This will cause the posterior mitral valve leaflet to also move anteriorly so as to improve leaflet coaptation and thereby reduce (or completely eliminate) mitral valve regurgitation. Using standard visualization means (e.g. echocardiography or fluoroscopy), the exact position of the straight, substantially rigid elongated body may be adjusted so as to reduce (or completely eliminate) regurgitation in the mitral valve.

Figure 16:
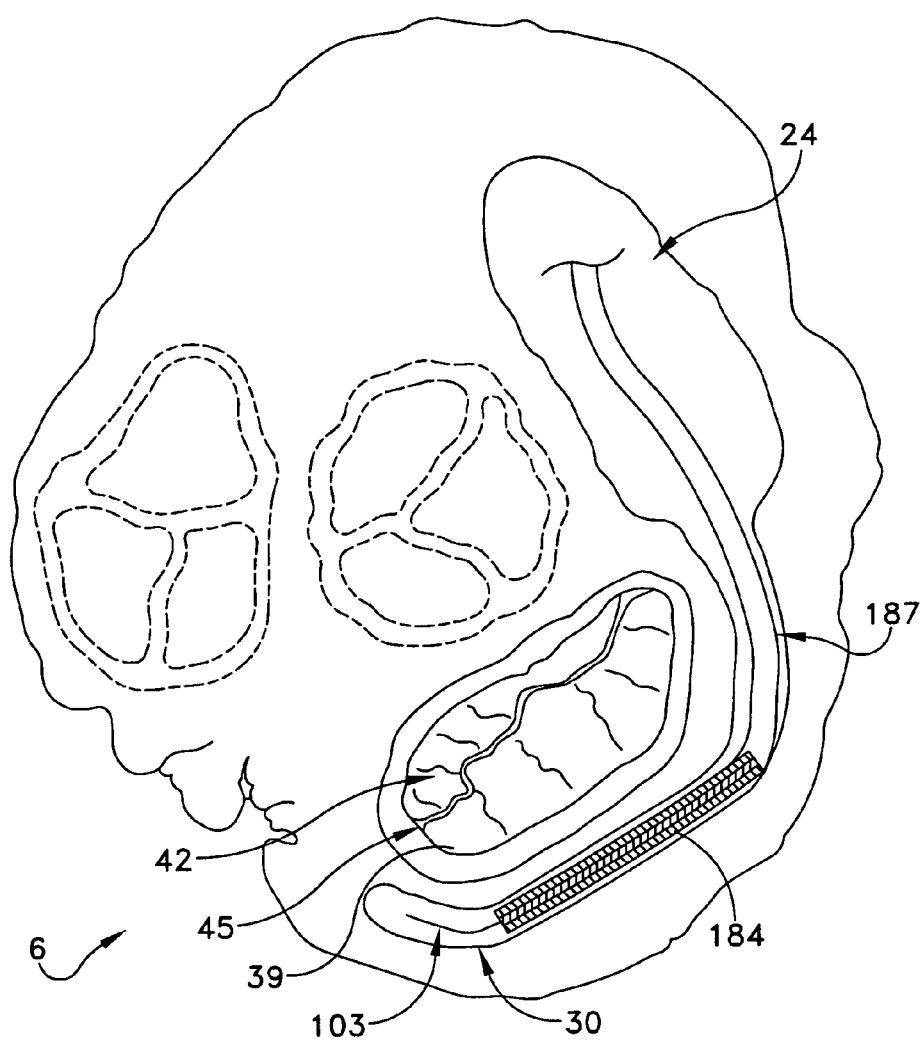
Figure 16A:
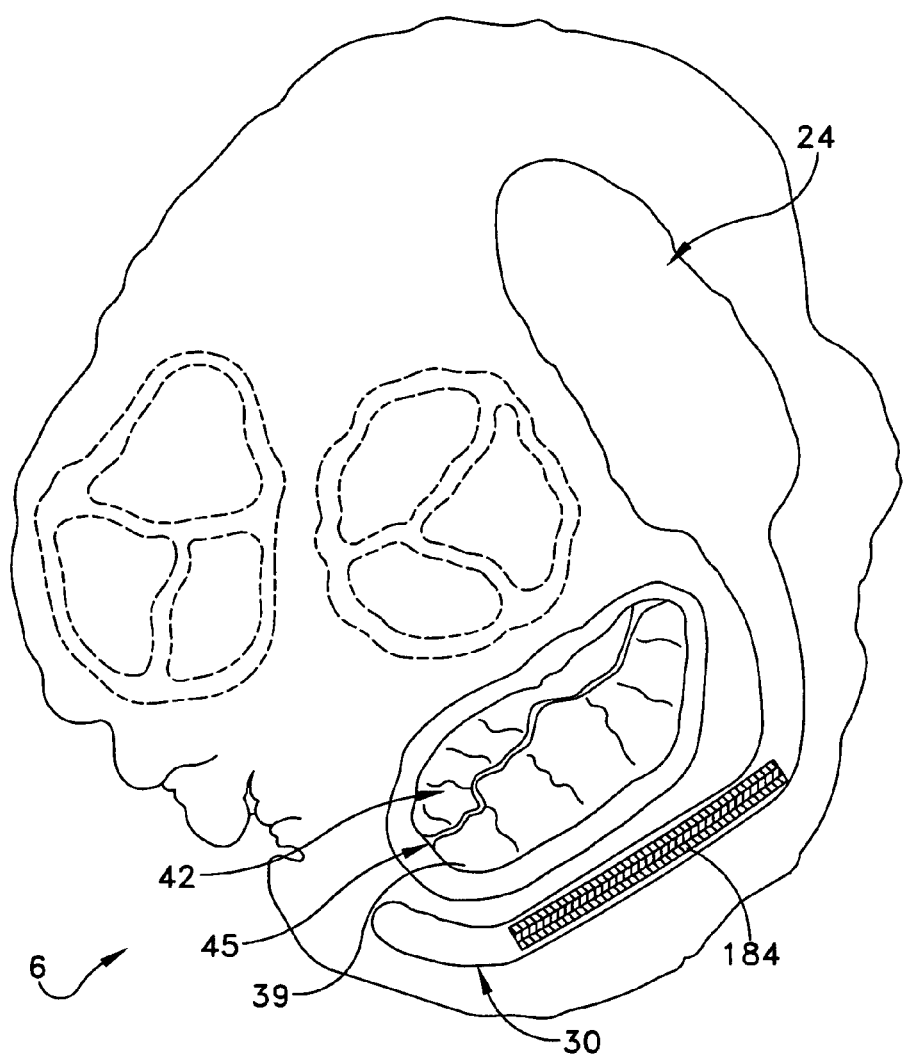
FIG. 16A illustrates another aspect of the present invention.
Figure 16B:
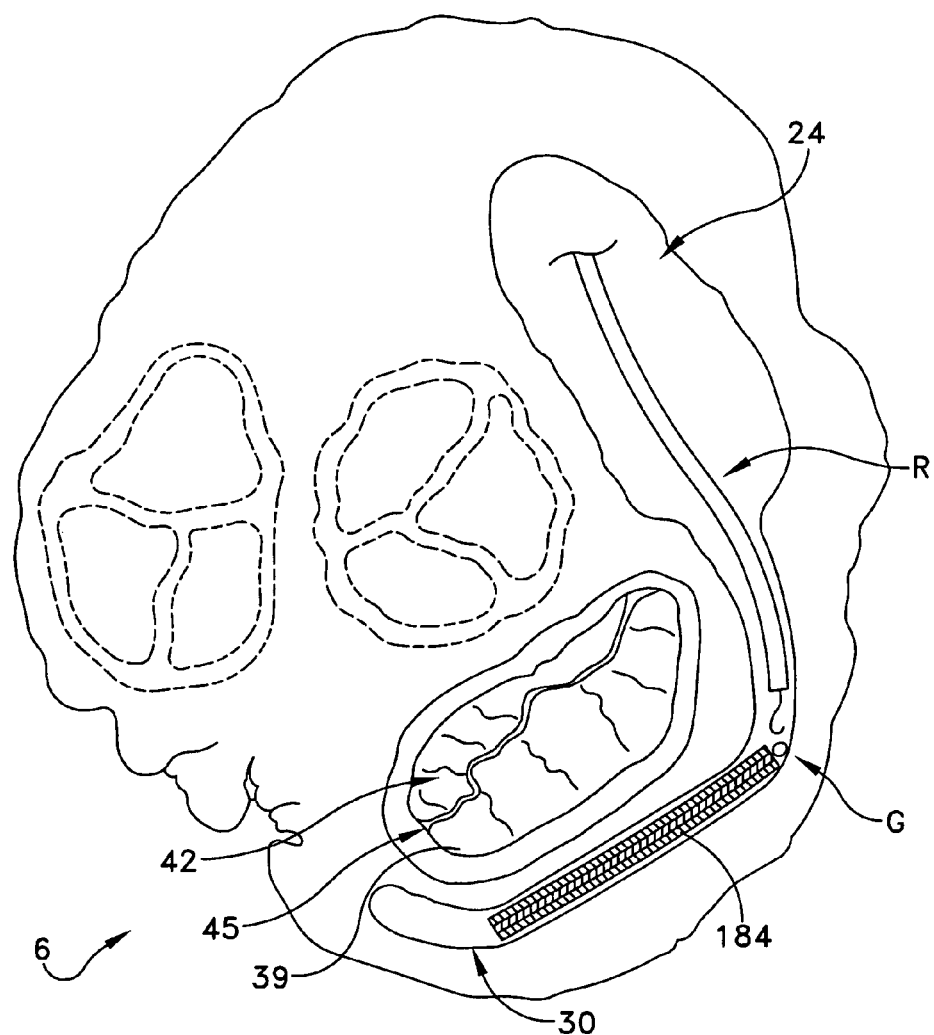
FIG. 16B illustrates still another aspect of the present invention.

If desired, the push cannula 187 may be provided with a releasably attachable interface (e.g., a grasper) so that it may releasably secure the proximal end 190 of the straight, substantially rigid elongated body 184. Such a feature will permit the straight, substantially rigid elongated body to be pulled backward within the coronary sinus, either for positioning or removal purposes.

Where elongated body 184 is to be left within the body for a substantial period of time, it is possible to leave the apparatus in the position shown in FIG. 16, i.e., with elongated body 184 fit over guidewire 103 and at the end of push cannula 187. Alternatively, guidewire 103 and/or push cannula 187 may be removed, leaving just elongated body 184 deployed at the surgical site (FIG. 16A). To the extent that elongated body 184 may be left by itself at the surgical site, it may be desirable to provide elongated body 184 with an eyelet or hook or other graspable feature G (FIG. 16B) such that a retriever R may thereafter be used to easily grapple and extract the elongated body 184 from the surgical site.

Figure 17:
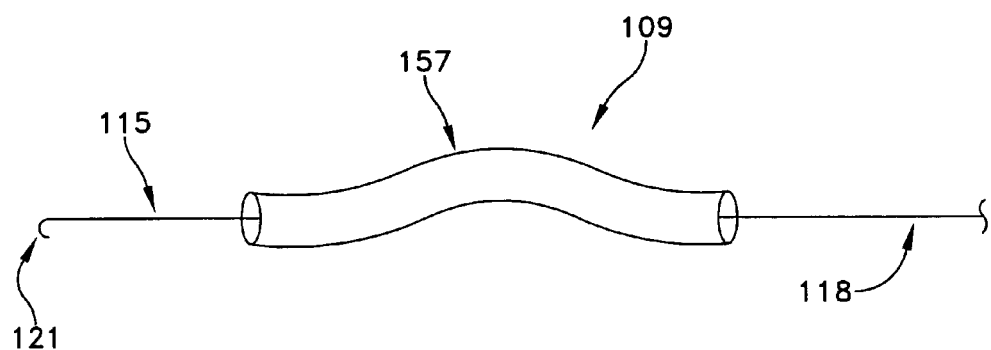
FIGS. 17–20 illustrate still other aspects of the present invention.
Figure 18:
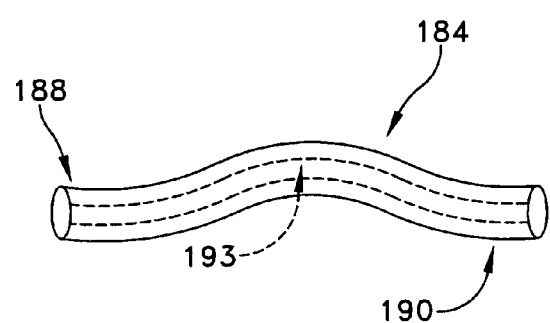
Figure 19:
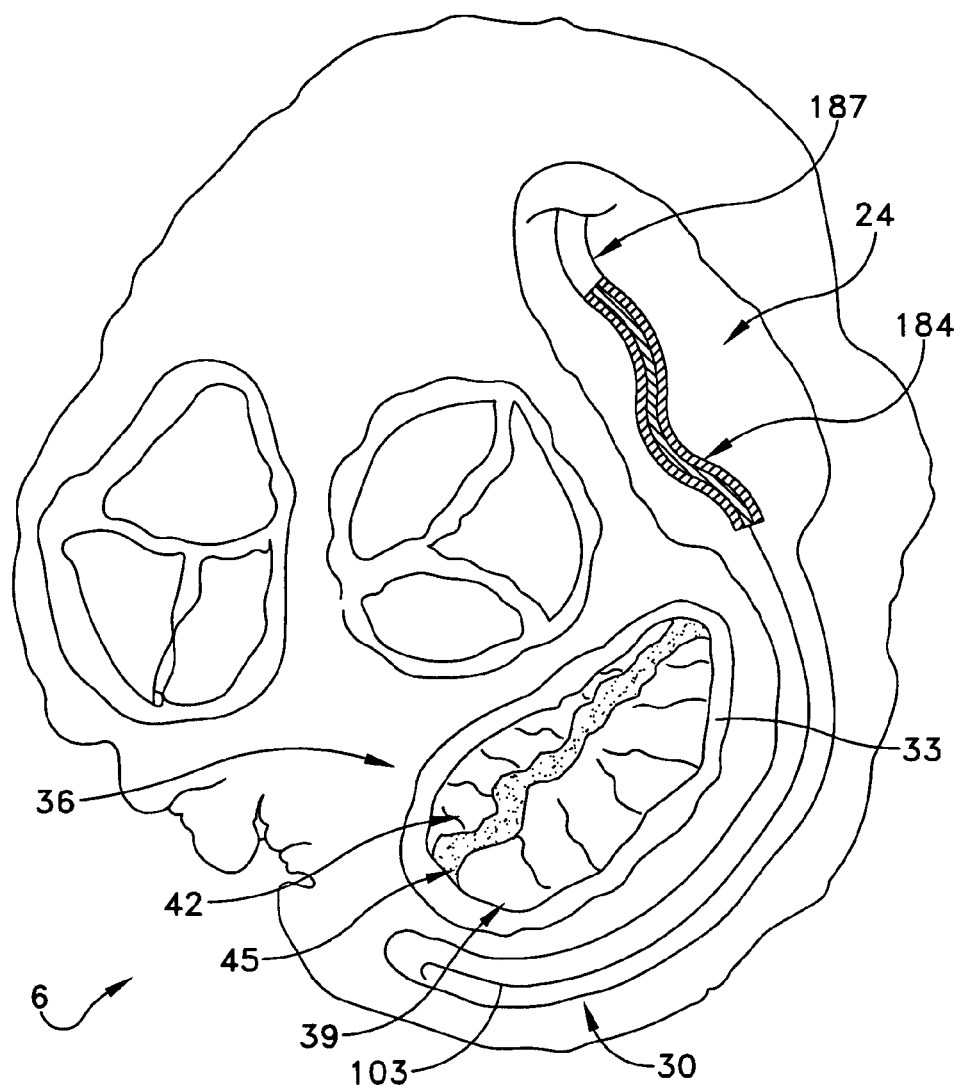
Figure 20:
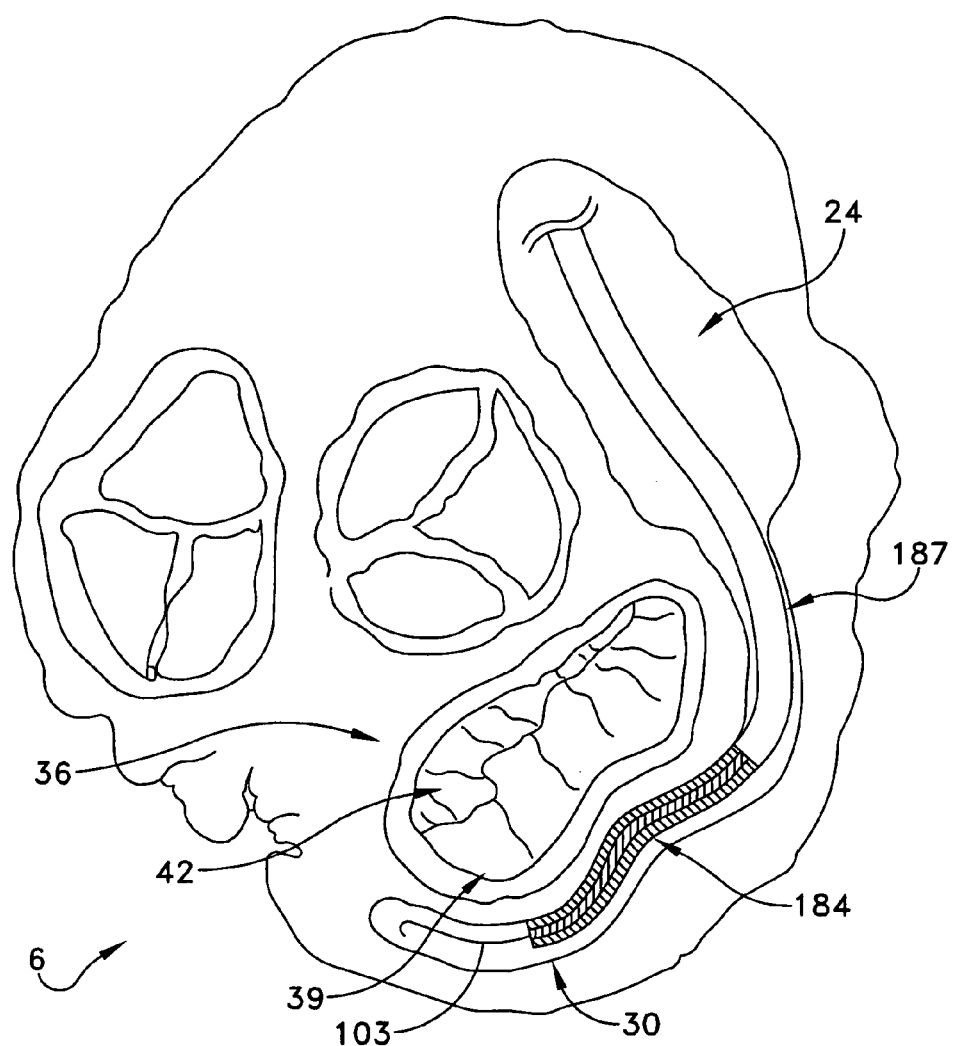

Elongated body 157 and/or elongated body 184 may have any of a variety of non-straight shapes along its length. For example, the elongated body may be wavy, spiraled, or curved along all or a portion of its length. By way of example, elongated body 157 and/or 184 may have a curved configuration so as to invert the natural curvature of the coronary sinus, i.e., so that it is bowed towards the anterior annulus. Or the elongated body may have a compound shape along its length, e.g., it may have a sort of "w" shape, with the center of the "w" being directed towards the anterior annulus. See, for example, FIG. 17, which shows a push rod 109 having an elongated body 157 with a "w" type of shape; and see FIG. 18, which shows an elongated body 184 with a "w" type of shape. See also FIGS. 19 and 20, which show a "w" shaped elongated body 184 being advanced down guidewire 103 (FIG. 19) to a position adjacent to mitral valve 36 (FIG. 20), whereby to reduce mitral regurgitation. Any of the aforementioned elongated body shapes, or other alternative shapes, may effect the anterior displacement of the posterior annulus that results in reduction of the mitral valve regurgitation.

Figure 22:
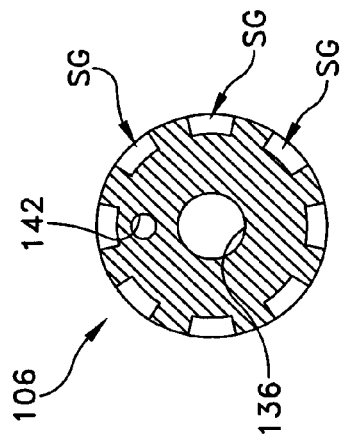
FIGS. 21–24 illustrate other aspects of the present invention.
Figure 24:
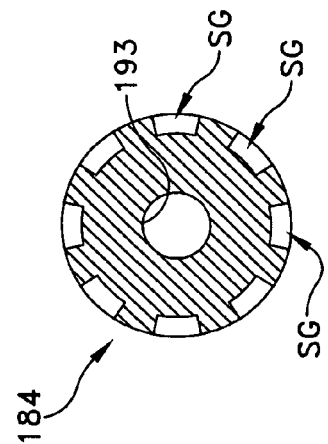
Figure 21:
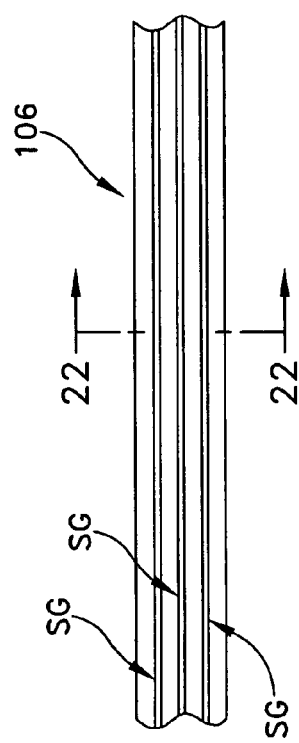
Figure 23:
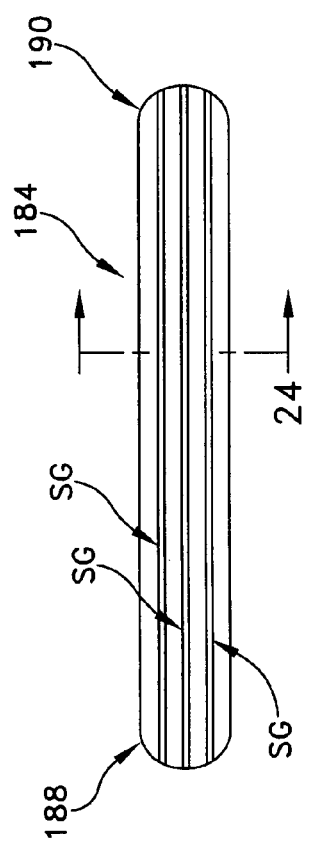

It is preferable that use of the present invention not result in occlusion of coronary sinus 30. Thus, with system 100 shown in FIG. 3, delivery catheter 106 is preferably sized so as to have a diameter less than the diameter of coronary sinus 30, so that blood may flow about the perimeter of delivery catheter 106 when delivery catheter 106 is disposed in coronary sinus 30. Alternatively, and/or additionally, and looking now at FIGS. 21 and 22, delivery catheter 106 may be provided with one or more longitudinally-extending surface grooves SG so as to facilitate blood flow past the perimeter of delivery catheter 106. Similarly, with system 181 shown in FIG. 12, elongated body 184 is preferably sized so as to have a diameter less that the diameter of coronary sinus 30, so that blood may flow about the perimeter of elongated body 184 when elongated body 184 is disposed in coronary sinus 30. Alternatively, and/or additionally, and looking now at FIGS. 23 and 24, elongated body 184 may be provided with one or more longitudinally-extending surface grooves SG so as to facilitate blood flow past the perimeter of elongated body 184.

In system 100 (FIG. 3) and in system 181 (FIG. 12), the elongated bodies 157 and 184 are shown completely formed prior to their deployment in the patient. However, it is also possible to form elongated body 157 and/or elongated body 184 in situ from a plurality of smaller elements.

Thus, for example, in FIGS. 25–27 there is shown an alternative form of push rod 109 for use with guidewire 103 and delivery catheter 106. More particularly, push rod 109 comprises flexible body 148 and a plurality of substantially rigid elongated elements 157A, 157B, 157C, etc. which collectively form the complete elongated body 157. Preferably the distalmost elongated element 157A is fixed to flexible body 148 while the remaining elongated elements 157B, 157C, 157D, etc. are free to slide on flexible body 148. In addition, elongated elements 157A, 157B, 157C, etc. preferably include connectors C for permitting one elongated element to be secured to a neighboring elongated body. The connectors C shown in FIG. 25 comprise male and female screw type connectors; however, other types of connectors may also be used.

By assembling the elongated body 157 in situ using a plurality of elongated elements 157A, 157B, 157C, etc., it is possible to create an elongated body 157 which is perfectly sized to the needs of the patient.

Figure 28:
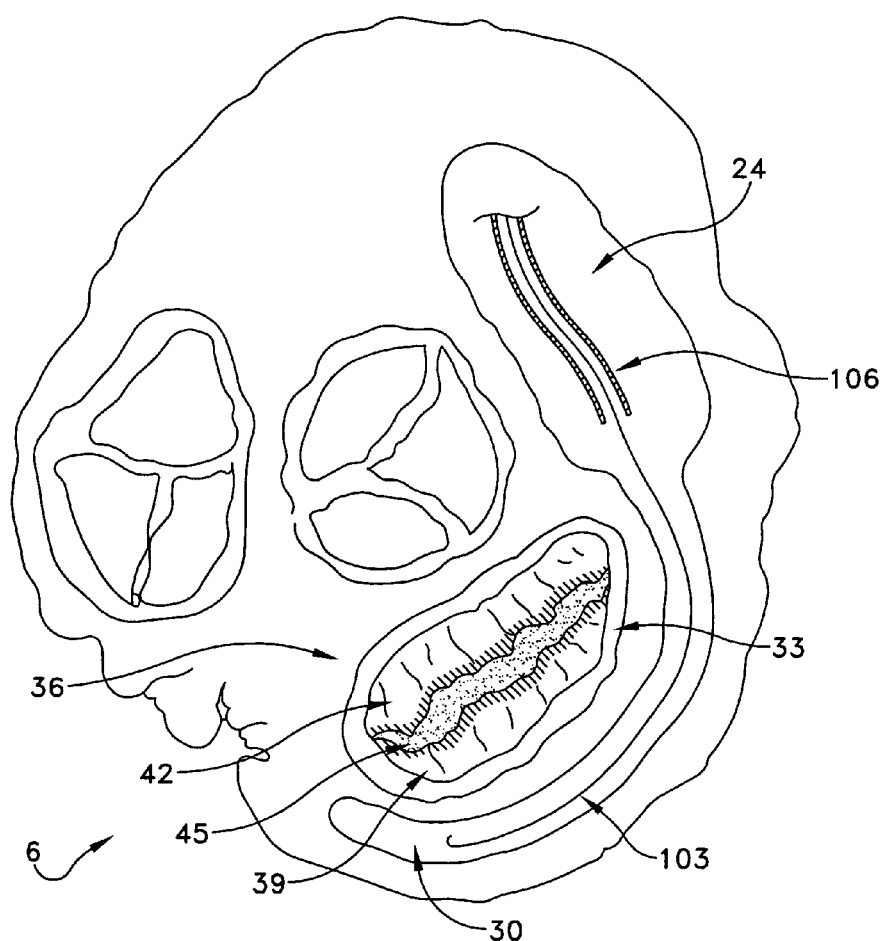
FIGS. 28–32 illustrate the embodiment of FIGS. 25–27 in use.
Figure 29:
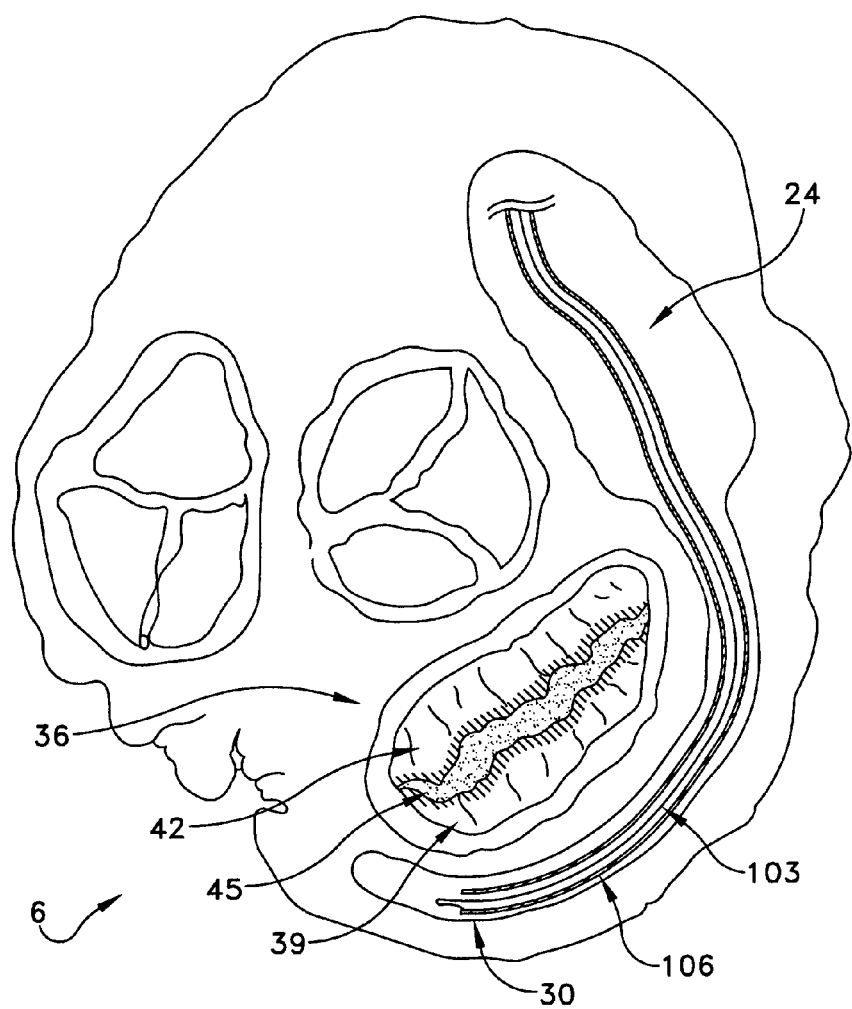
Figure 30:
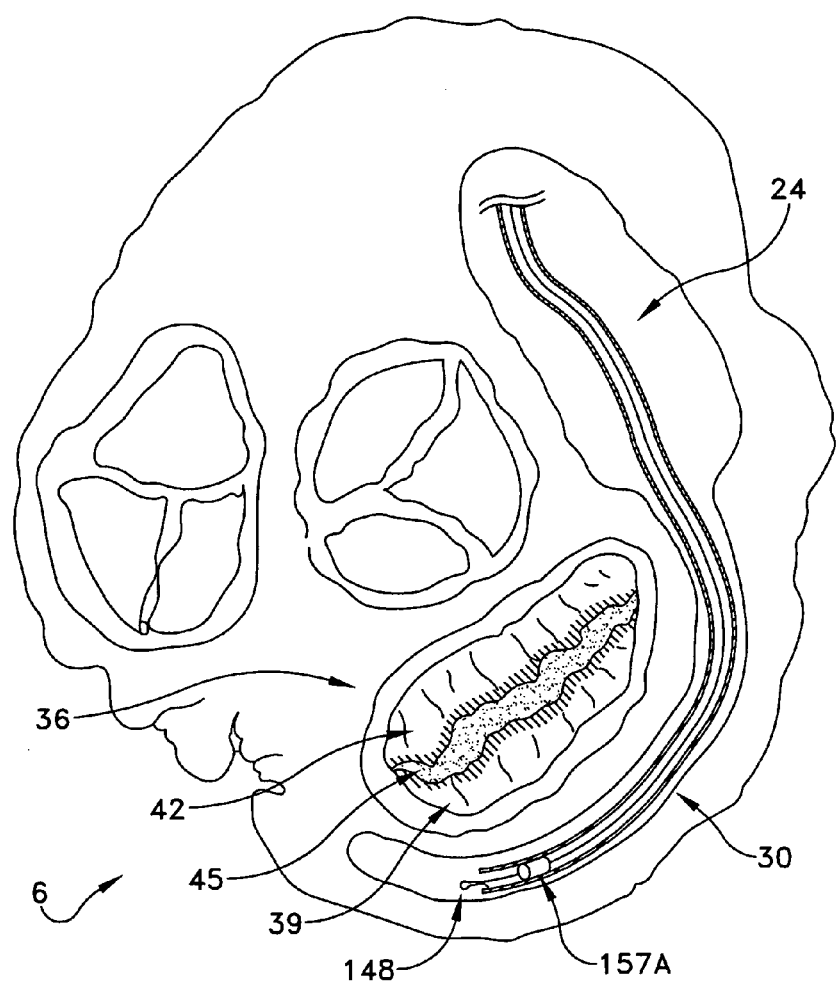
Figure 31:
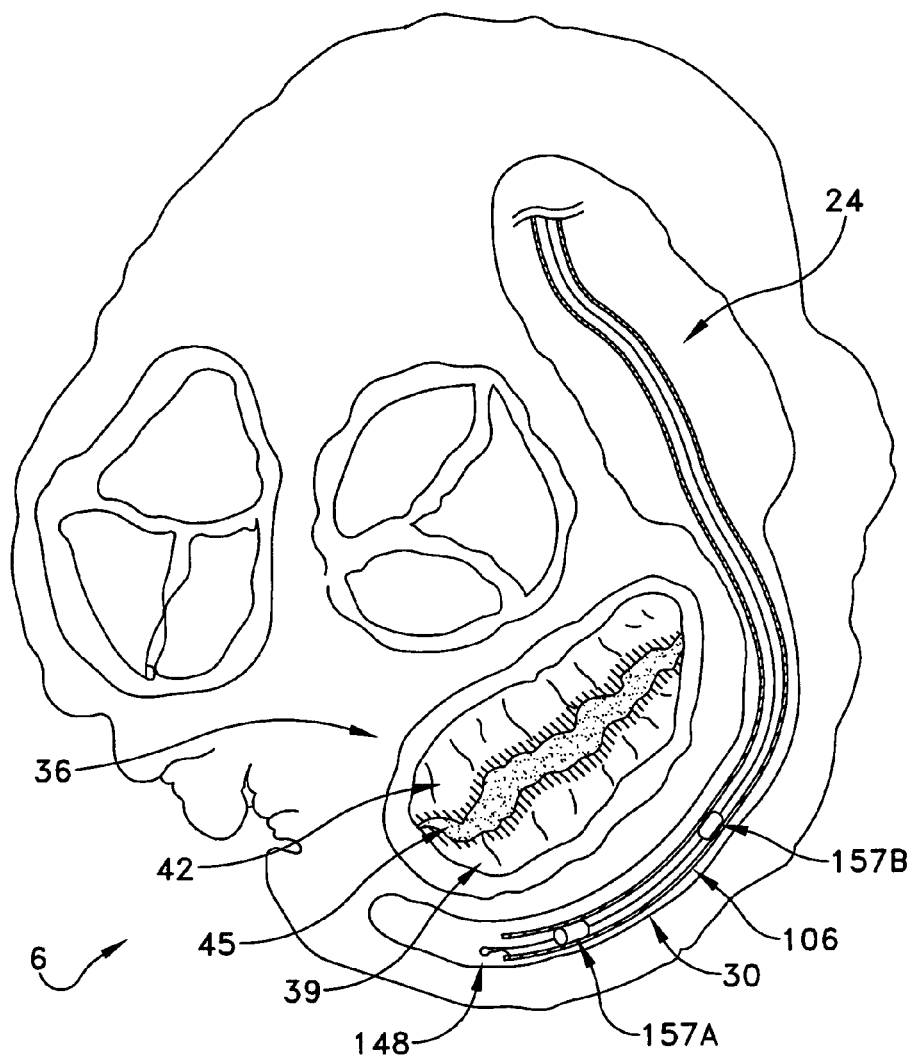

The push rod 109 shown in FIGS. 25–27 may be used as follows. First, guidewire 103 is passed down to the coronary sinus (FIG. 28). Then delivery catheter 106 is passed down guidewire 103 and into the coronary sinus (FIGS. 28 and 29). Then the guidewire 103 is withdrawn from the surgical site and replaced by the push rod's flexible body 148 with elongated element 157A attached (FIG. 30). Next, a plurality of elongated elements 157B, 157C, 157D, etc. are slid down flexible body 148 (FIG. 31) and secured to elongated element 157A (and any preceding elongated element). As many elongated elements 157A, 157B, 157C, etc. are used as is necessary to effect the desired leaflet coaptation (FIG. 32).

In FIGS. 32A–32C, there is shown another form of push rod 109. More particularly, with this form of the push rod, elongated body 157 is formed by a plurality of elongated elements 157A, 157B, 157C, etc. which collectively form the complete elongated body 157. Preferably the distalmost elongated element 157A is fixed to flexible body 148 while the remaining elongated elements 157A, 157B, 157C, etc. are free to slide on flexible body 148. With this version of the invention, elongated body 157 may be formed in situ by moving elongated elements 157A, 157B, 157C, etc. distally, with distalmost elongated element 157A acting as a distal stop, and then keeping elongated elements 157A, 157B, 157C, etc. biased distally with a holding mechanism, e.g., a crimp CR.

Figure 32:
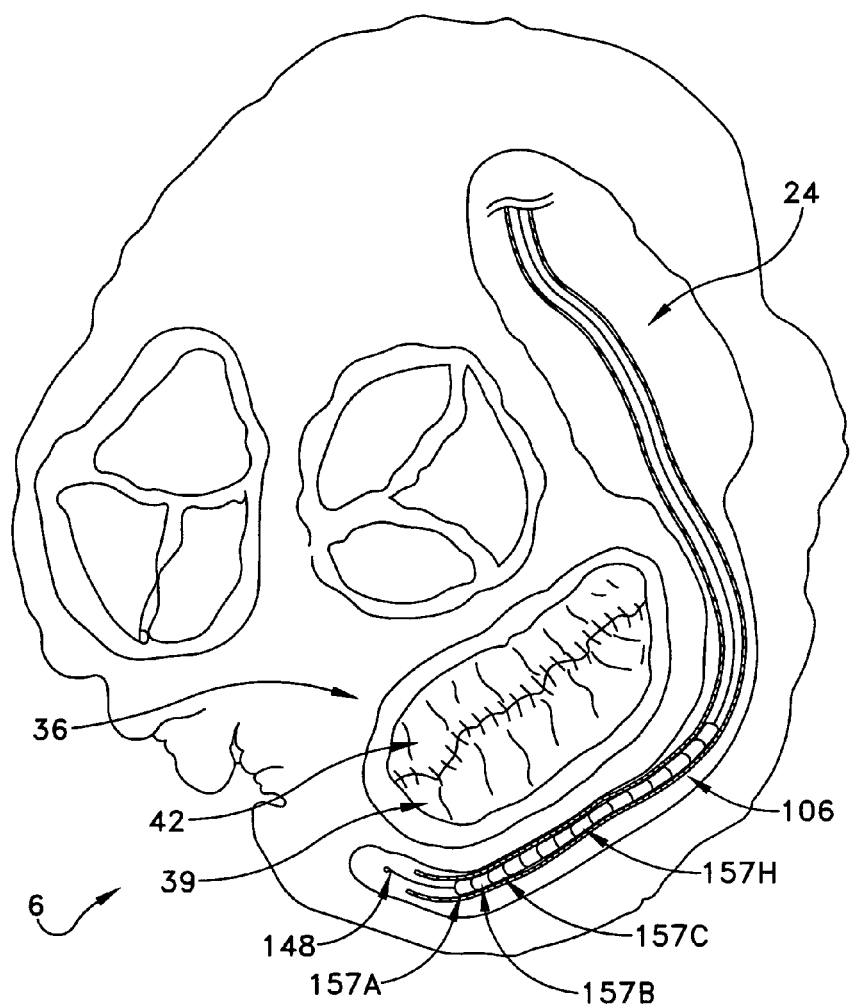
Figure 32D:
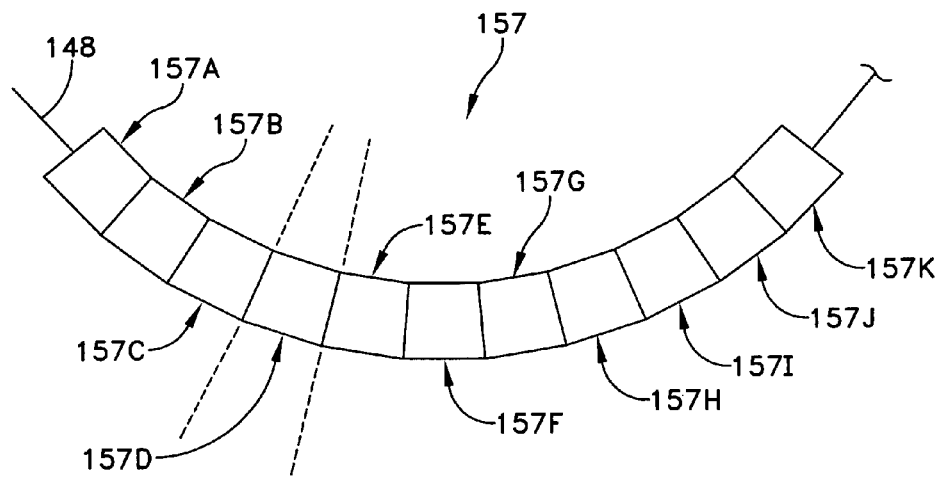
FIGS. 32D and 32E illustrate another aspect of the present invention.
Figure 32E:
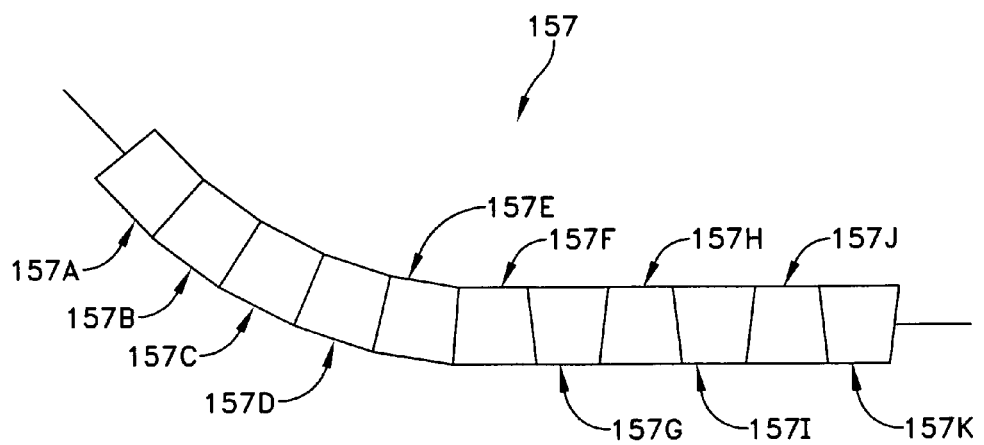

In FIGS. 25–32, and in FIGS. 32A–32C, elongated elements 157A, 157B, 157C, etc. are shown configured so as to form a substantially straight elongated body 157. However, if desired, elongated elements 157A, 157B, 157C, etc. could have alternative configurations so as to form other body shapes. Thus, for example, in FIG. 32D elongated elements 157A, 157B, 157C, etc. are shown forming a curved elongated body 157, and in FIG. 32E elongated elements 157A, 157B, 157C, etc. are shown forming a composite curved-and-straight elongated body 157. It will be appreciated that still other shapes may be formed by elongated elements 157A, 157B, 157C, etc. In this respect it will be appreciated that the shapes of elongated body 157 may be established either by (1) forming elongated elements 157A, 157B, 157C, etc. so that they have only one possible way of being assembled together, or (2) by forming elongated elements 157A, 157B, 157C, etc. so that they have multiple ways of being assembled together. In this latter situation, one possible way to vary the final configuration of elongated body 157 is by individually rotating various ones of elongated elements 157A, 157B, 157C, etc., e.g., such as is shown in FIGS. 32D and 32E.

As noted above, it is also possible to form the elongated body 184 of system 181 (FIG. 12) in situ from a plurality of smaller elements.

Figure 33:
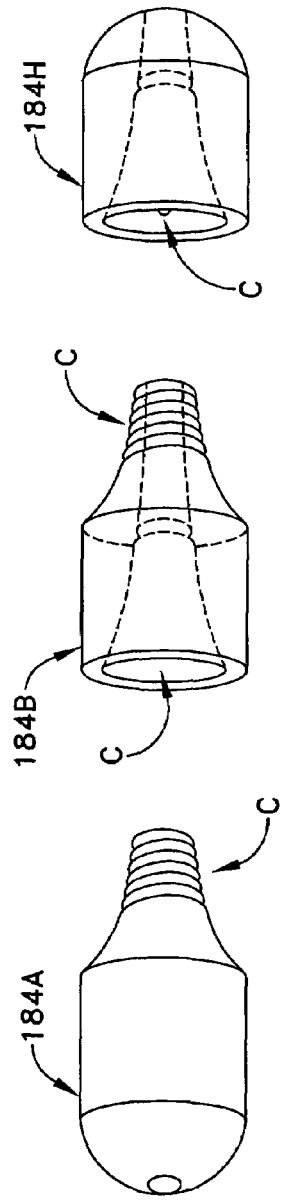
FIGS. 33 and 34 illustrate another form of the present invention.
Figure 34:
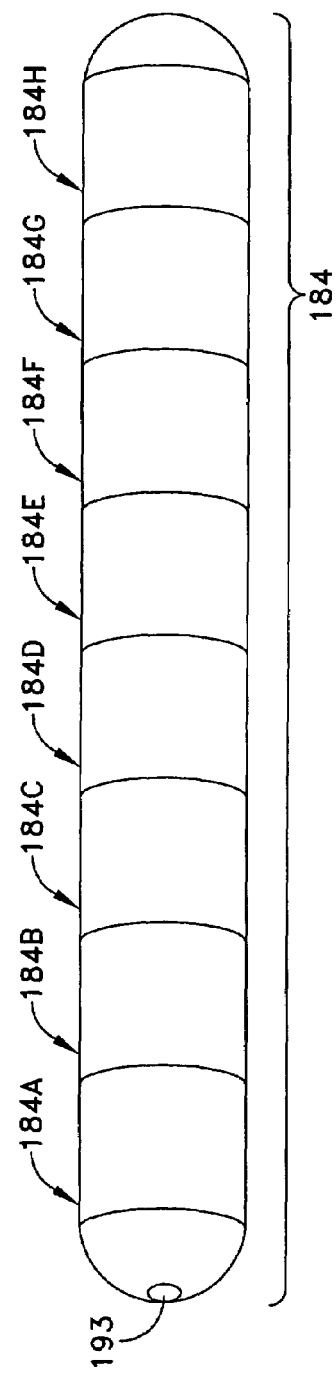

Thus, for example, in FIGS. 33 and 34 there is shown an alternative form of elongated body 184 which comprises a plurality of substantially rigid elongated elements 184A, 184B, 184C, etc. which collectively form the complete elongated body 184. In addition, elongated elements 184A, 184B, 184C, etc. preferably include connectors C for permitting one elongated element to be secured to a neighboring elongated element. The connectors C shown in FIG. 25 comprise male and female screw type connectors; however, other types of connectors may also be used.

By assembling the elongated body 184 in situ using a plurality of elongated elements 184A, 184B, 184C, etc., it is possible to create an elongated body 184 which is perfectly sized to the needs of the patient.

Figure 35:
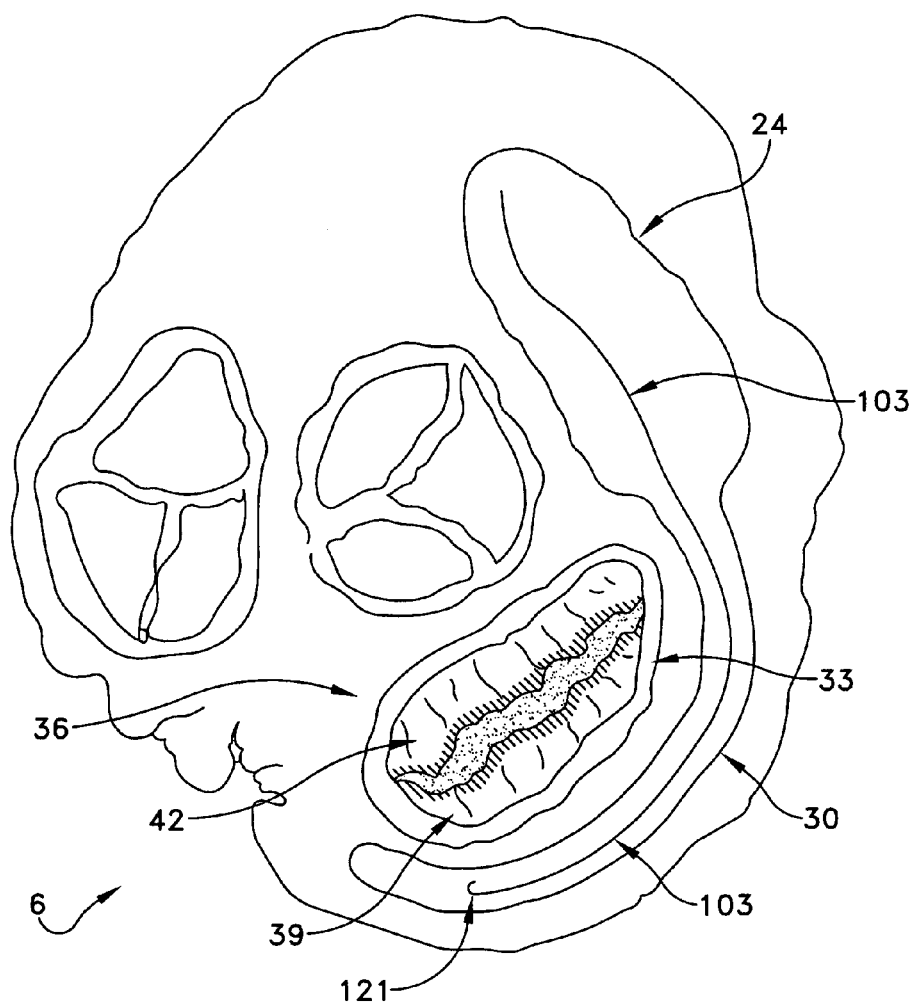
FIGS. 35–37 illustrate the embodiment of FIGS. 33 and 34 in use.
Figure 36:
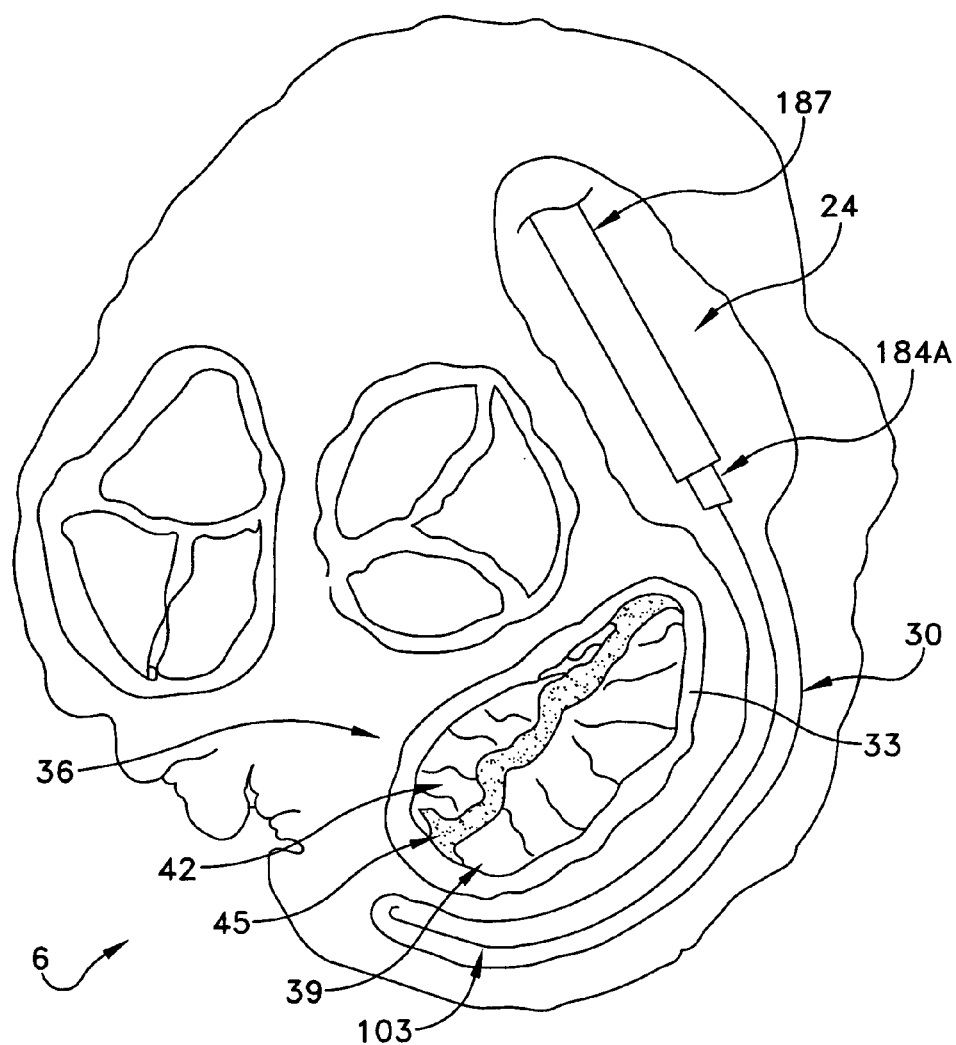
Figure 37:
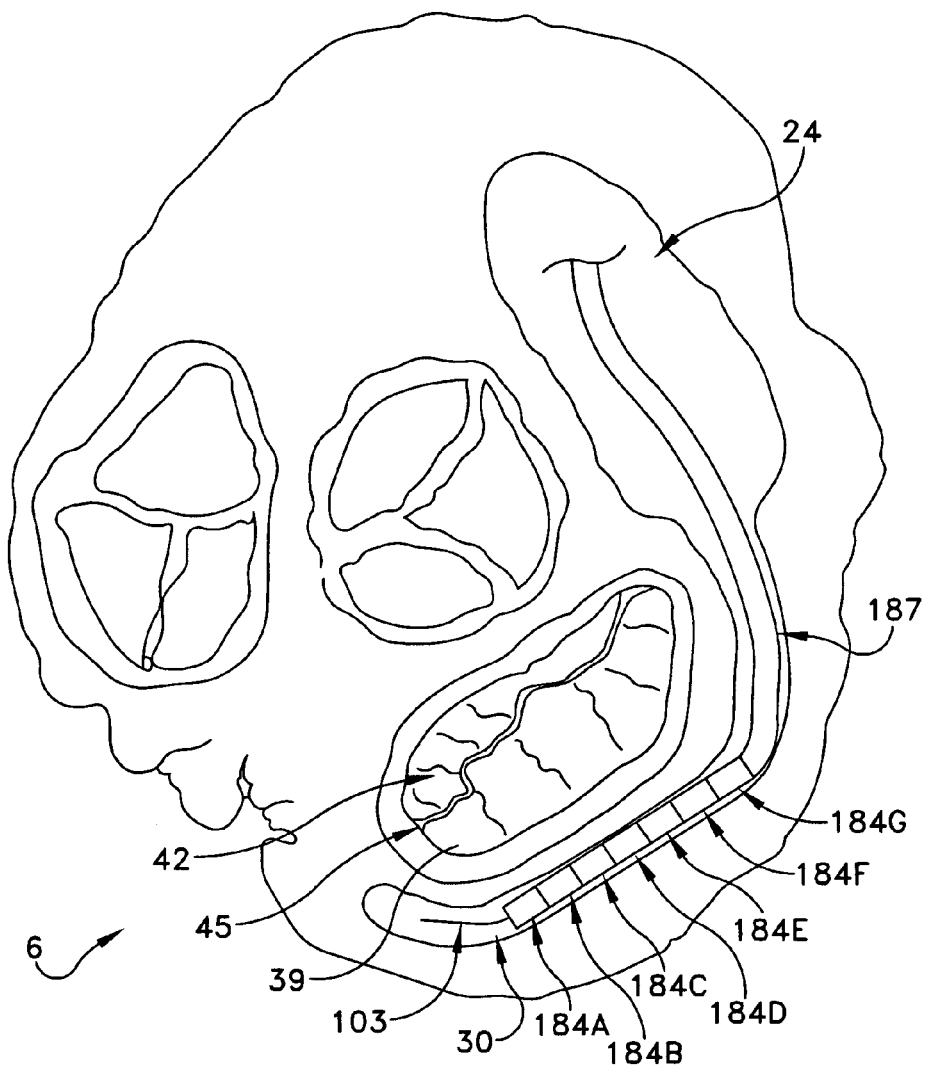

The elongated body 184 shown in FIGS. 33 and 34 may be used as follows. First, guidewire 103 is passed down coronary sinus 30 (FIG. 35). Then push cannula 187 is used to push a plurality of elongated elements 184A, 184B, 184C, etc. down guidewire 103 and into the coronary sinus (FIGS. 36 and 37). As many elongated elements 184A, 184B, 184C, etc. are used as is necessary to effect the desired leaflet coaptation (FIG. 37).

In FIGS. 37A–37C, there is shown another form of elongated body 184. More particularly, with this form of elongated body, the elongated body 184 is formed by a plurality of elongated elements 184A, 184B, 184C, etc. which collectively form the complete elongated body 184. Preferably, all of the elongated elements 184A, 184B, 184C, etc. are free to slide on guidewire 103. With this version of the invention, elongated body 184 may be formed in situ by moving elongated elements 184A, 184B, 184C, etc. distally and then drawing them tightly together, e.g., such as by using a cinching system such as that shown in FIG. 37C and comprising a distal member DM and a crimp CR.

Figure 37D:
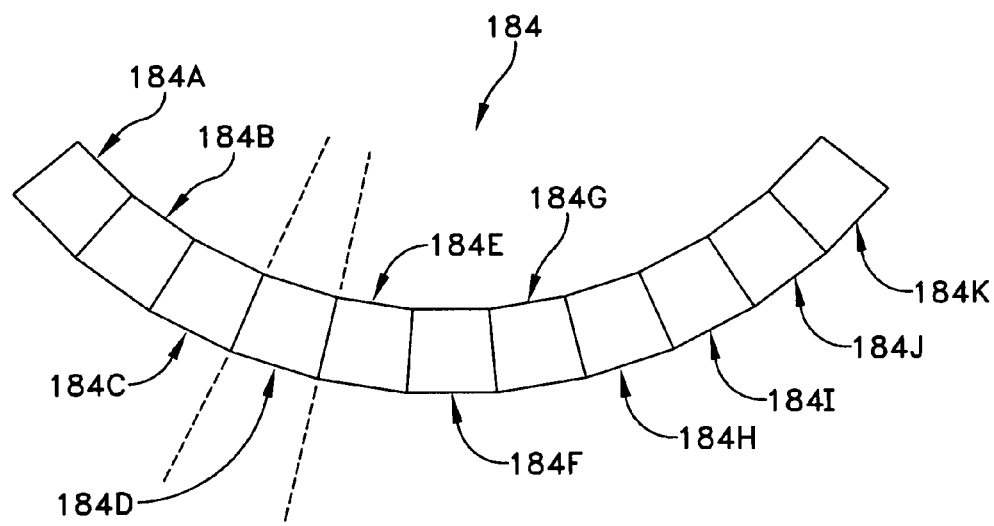
FIGS. 37D and 37E illustrate another aspect of the present invention.
Figure 37E:
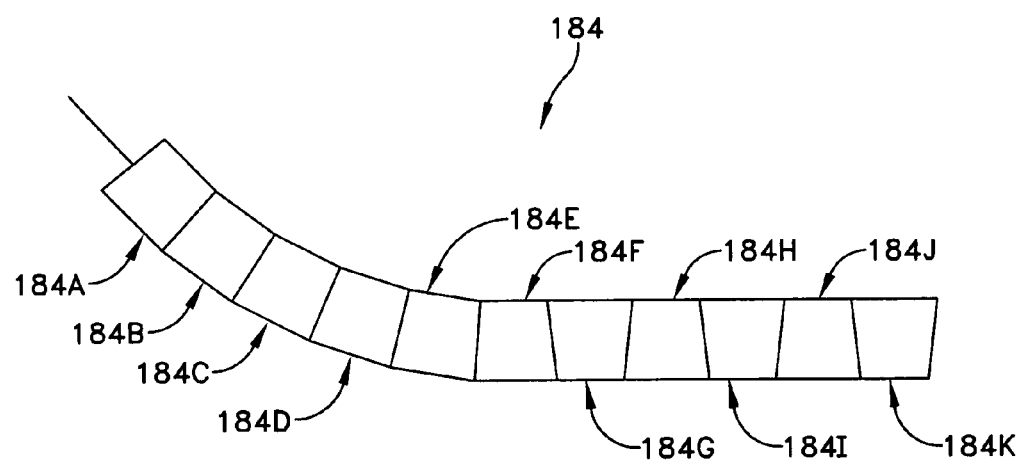

Again, in FIGS. 33–37, and in FIGS. 37A–37C, elongated element 184A, 184B, 184C, etc. are shown configured so as to form a substantially straight elongated body 184. However, if desired, elongated elements 184A, 184B, 184C, etc. could have alternative configurations so as to form other body shapes. Thus, for example, in FIG. 37D elongated elements 184A, 184B, 184C, etc. are shown forming a curved elongated body 184, and in FIG. 37E elongated elements 184A, 184B, 184C, etc. are shown forming a composite curved-and-straight elongated body 184. It will be appreciated that still other shapes may be formed by elongated elements 184A, 184B, 184C, etc. In this respect it will be appreciated that the shapes of elongated body 184 may be established either by (1) forming elongated elements 184A, 184B, 184C, etc. so that they have only one possible way of being assembled together, or (2) by forming elongated elements 184A, 184B, 184C, etc. so that they have multiple ways of being assembled together. In this latter situation, one possible way to vary the final configuration of elongated body 184 is by individually rotating various ones of elongated elements 184A, 184B, 184C, etc., e.g., such as is shown in FIGS. 37D and 37E.

Looking next at FIGS. 37F–37I, there is shown a straightening device 109A, which is another form of push rod 109, and straightening apparatus 109A has an elongated body 157 formed by a plurality of elongated elements 157A, 157B, 157C, etc. Each of the elongated elements 157A, 157B, 157C, etc. is attached to flexible body 148 and is separated from adjacent elongated elements by a gap G. By orienting gaps G radially away from mitral valve 36 (FIG. 37H), straightening apparatus 109A will be able to curve as required so as to follow the natural curvature of the coronary sinus, e.g., during insertion of push rod 109 into coronary sinus 30. However, by rotating flexible body 148 about its axis so that gaps G are oriented 180 degrees opposite to that shown in FIG. 37H (i.e., as shown in FIG. 37I), gaps G will be closed and straightening apparatus 109A will be straightened, whereby to apply an anteriorly-directed force to the posterior annulus of mitral valve 36 and reduce mitral regurgitation.

Figure 37J:
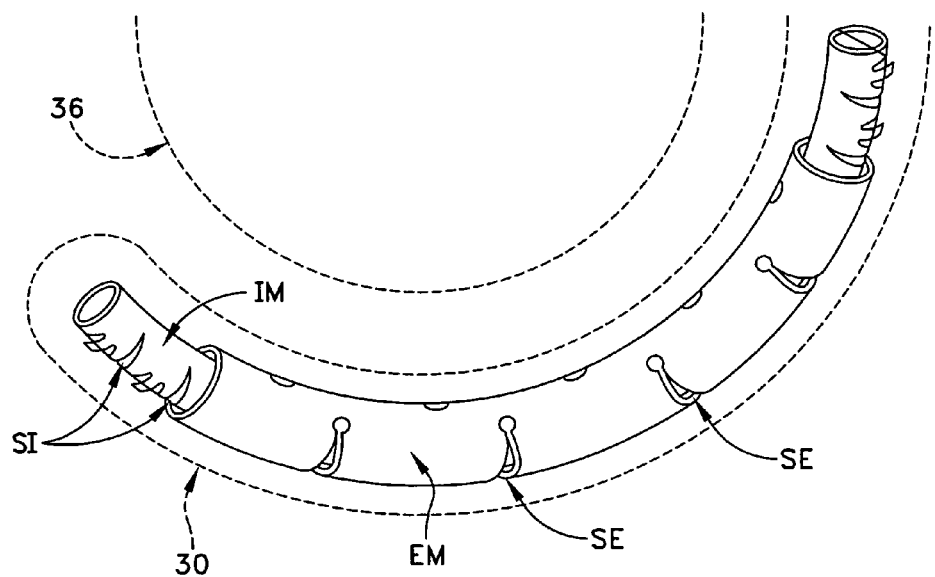
FIGS. 37J and 37K illustrate yet another aspect of the present invention.
Figure 37K:
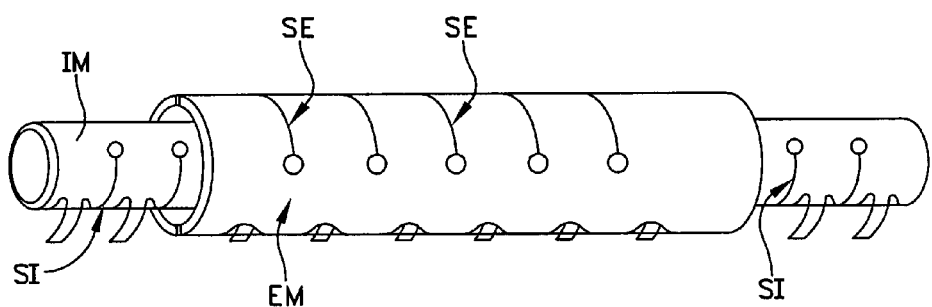

Looking next at FIGS. 37J and 37K, there is shown another form of the invention. In this construction, an internal member IM has a plurality of slots SI and an external member EM has a plurality of slots SE. Internal member IM is concentrically received within external member EM. By orienting internal member IM and external member EM so that slots SI are aligned with slots SE (FIG. 37J), internal member IM and external member EM may be curved as required so as to follow the natural curvature of the coronary sinus, e.g. during insertion of the members into the coronary sinus. However, by orienting internal member IM and external member EM so that slots SI are oriented away from slots SE (FIG. 37K), internal member IM and external member EM will be straightened, whereby to apply an anteriorly-directed force to the posterior annulus of the mitral valve and reduce mitral regurgitation.

It is also possible to form elongated body 157 of push rod 109 (FIG. 3) with an inflatable construction. More particularly, and looking next at FIG. 38, there is shown a push rod 109 having an inflatable elongated body 157 in the form of a balloon B. The push rod's flexible body 148 includes an inflation lumen L which communicates with the interior of balloon B, whereby fluid may be supplied to the interior of the balloon so as to inflate the balloon. The balloon B is constructed so that it has a flexible configuration when it is in a deflated condition and an elongated, straight configuration when it is in an inflated condition.

Figure 4:
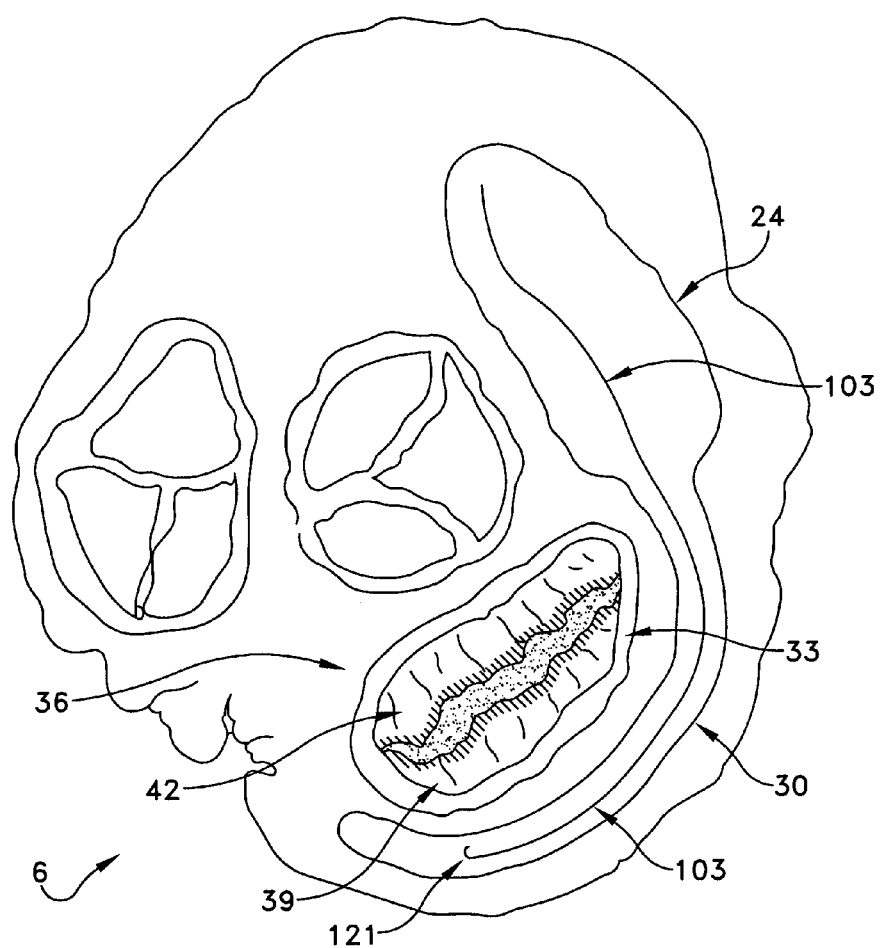
FIGS. 4–7 are a series of views illustrating use of the system of FIG. 3 to reduce mitral regurgitation.
Figure 5:
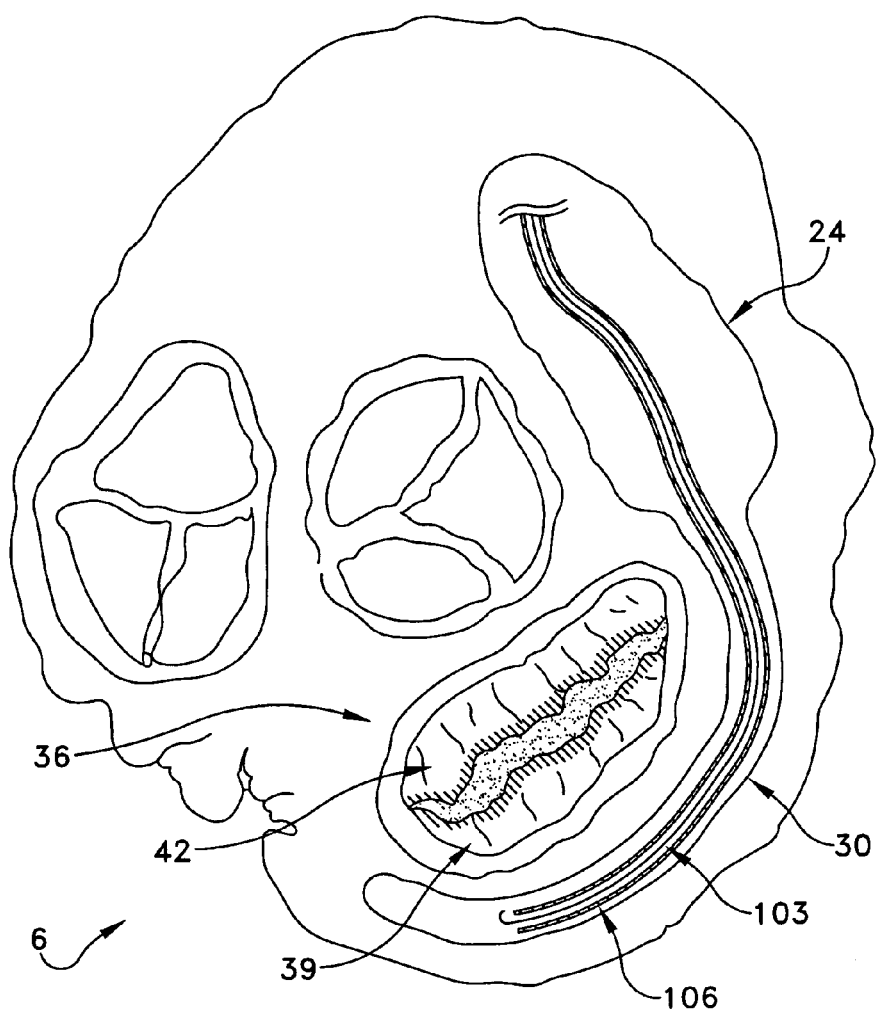
Figure 6:
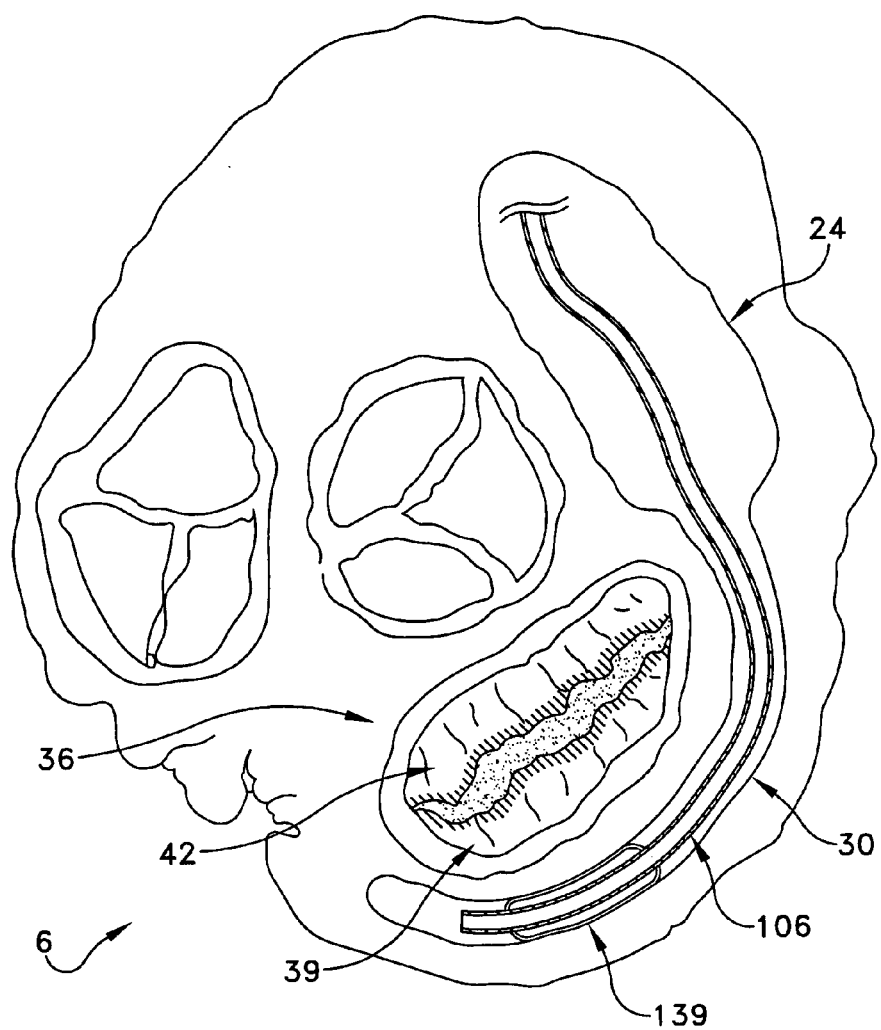
Figure 39:
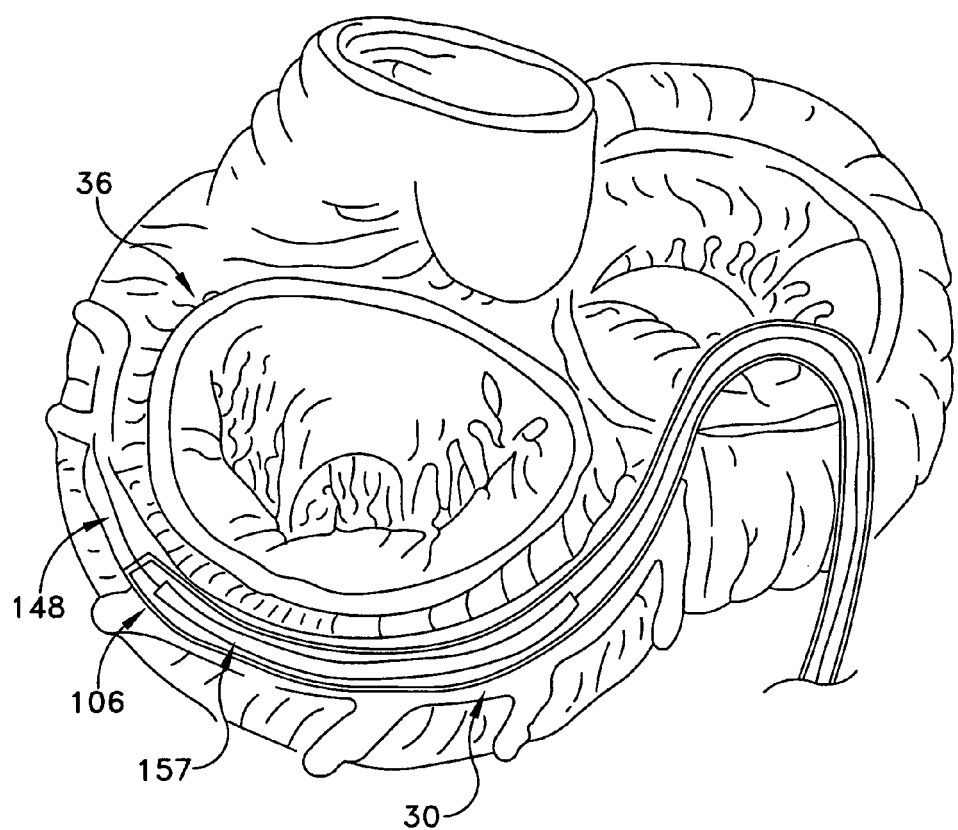
FIGS. 39 and 40 illustrate the embodiment of FIG. 38 in use.
Figure 40:
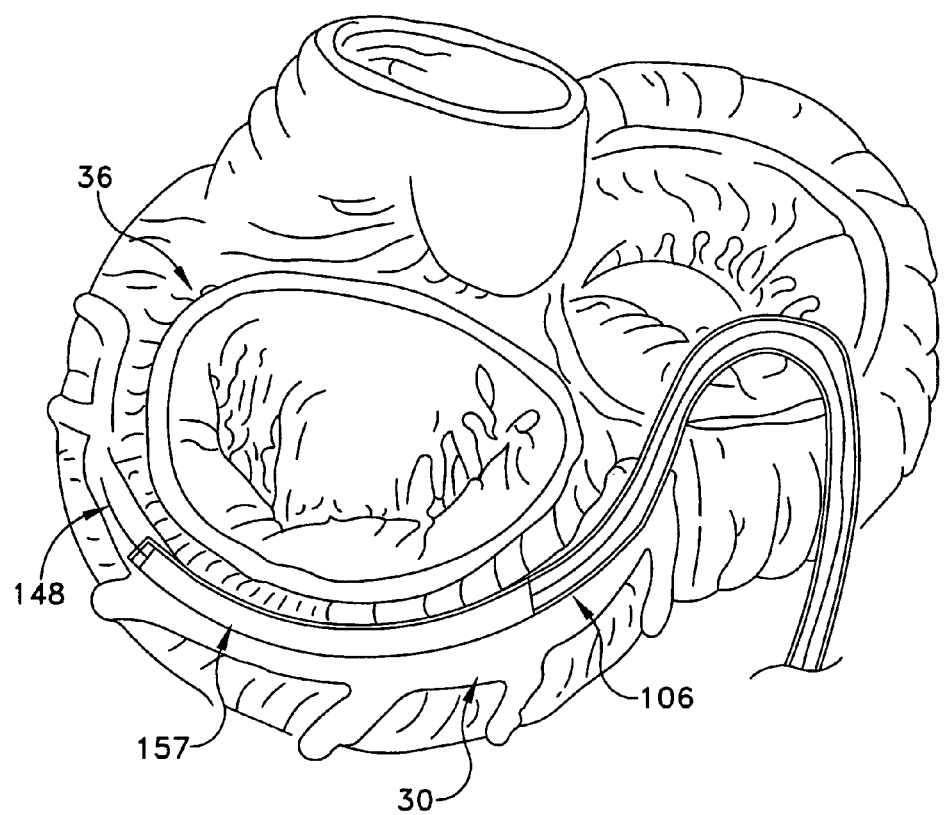

The push rod 109 of FIG. 38 may be used as follows. First, guidewire 103 is advanced into the coronary sinus 30 (FIG. 4). Then delivery cannula 106 is advanced over guidewire 103 until the distal end of the delivery cannula is in coronary sinus 30 (FIG. 5). Next, guidewire 103 is withdrawn (FIG. 6). Then push rod 109, with elongated body 157 in a deflated condition, is advanced along the interior of delivery cannula 106 so that balloon B is adjacent to the mitral valve (FIG. 39). Then balloon B is inflated, using inflation lumen L, so that elongated body assumes its elongated, straightening configuration (FIG. 40). As this occurs, the posterior annulus of the mitral valve is compressed anteriorly, so as to reduce mitral regurgitation.

It is also possible to form an inflatable elongated body 157 of push rod 109 with other configurations. By way of example, it is possible to form an inflatable body 157 with a piston-type configuration, whereby the body may be elongated or shortened as desired. More particularly, and looking now at FIGS. 41 and 42, inflatable body 157 may comprise a distal portion 157' and a proximal portion 157", with the distal and proximal portions being in a sliding, piston-like relationship. As a result, fluid may be supplied to the combined interiors of the distal and proximal portions, so as to force the two elements apart relative to one another. In use, the push rod 109 of FIGS. 41 and 42 is positioned in its "compressed" state (FIG. 41), passed down the interior of delivery cannula 106 until inflatable elongated body 157 is positioned adjacent to the mitral valve, and then inflated (using inflation lumen L) into its "expanded" state (FIG. 42). As this occurs, the naturally curved coronary sinus is straightened, thereby pushing the posterior annulus of the mitral valve anteriorly, whereby to reduce mitral regurgitation.

In addition to the foregoing, it should also be appreciated that with respect to push rod 109, the flexible body 148 may comprise an electrical lead for an implantable bi-ventricular pacing device and/or an electrical lead for an implantable cardio defibrillator device, etc. In this case, the distal end of flexible body 148 would be elongated somewhat and would not reside within the coronary sinus; rather, it would be positioned within the tissue which is to receive the electrical stimulus while elongated body 157 is positioned adjacent to the mitral valve. Such a construction would allow the bi-ventricular pacing device and/or the implantable cardio defibrillator device to work in conjunction with elongated body 157 to reduce mitral regurgitation.

It should also be appreciated that the function of hydraulic energy employed to enlarge inflatable body 157 may be substituted by a mechanical energy transformer such as a lead screw mechanism or an electromechanical solenoid.

In a corresponding fashion, the guidewire 103 over which elongated body 184 is deployed may also be in the form of an electrical lead for an implantable bi-ventricular pacing device and/or an electrical lead for an implantable cardio defibrillator device, etc. Again, in this case the distal end of the wire will be positioned within the tissue which is to receive the electrical stimulus while elongated body 184 is positioned adjacent to the mitral valve. Such a construction would allow the implantable bi-ventricular pacing device and/or the implantable cardio defibrillator device to work in conjunction with elongated body 157 to reduce mitral regurgitation.

Figure 43:
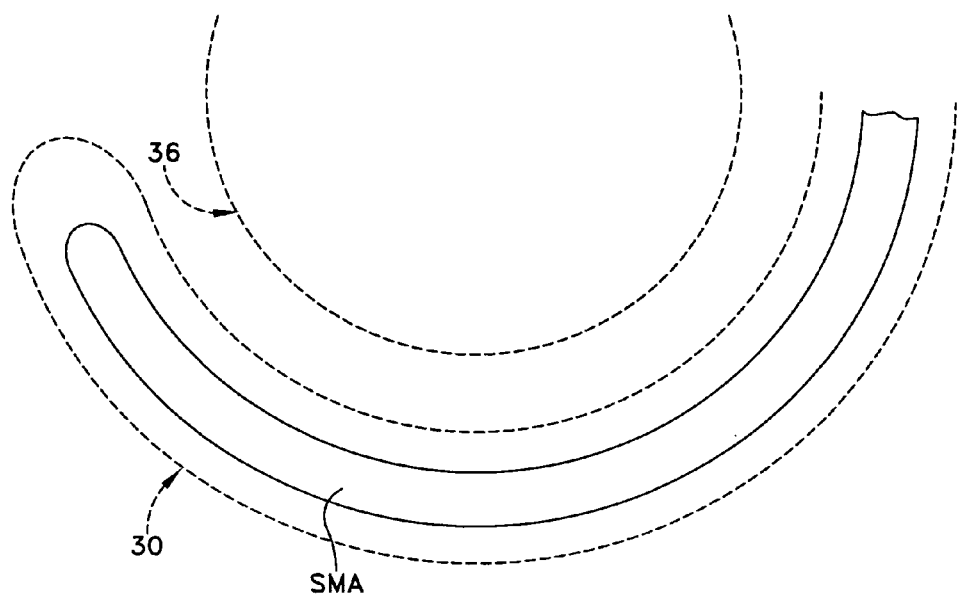
FIGS. 43 and 44 illustrate still another aspect of the present invention.
Figure 44:
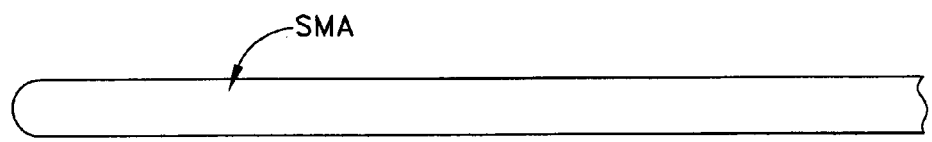

Looking next at FIGS. 43 and 44, there is shown yet another form of the present invention. In this form of the invention, there is provided an elongated shape memory alloy body SMA which is configured to be substantially flexible at a temperature $T_1$ and substantially rigid and in a straight configuration at another temperature $T_2$, where temperature $T_2$ is normal body temperature. In this situation, body SMA is brought to temperature $T_1$, so that it may be inserted more easily into the natural curvature of the coronary sinus, e.g., during insertion of body SMA into the coronary sinus (FIG. 43). However, when body SMA thereafter transitions to temperature $T_2$, body SMA will assume its straight configuration (FIG. 44), whereby to apply an anteriorly-directed force to the posterior annulus of the mitral valve and reduce mitral regurgitation. It will be appreciated that the configuration of body SMA may be other than straight (i.e., "w" shape, etc.) to best displace the posterior annulus anteriorly.

In other alternative embodiments, the elongated body may be flexible along at least a portion of its length. Regional flexibility and regional stiffness may allow for straightening of select locations of the coronary sinus and corresponding locations of the posterior mitral annulus. This can cause regions of the mitral annulus to move anteriorly, thus causing regional improvements in leaflet coaptation. In addition, the elongated body may be formed by two end segments connected together by a filament: by anchoring the two end segments relative to the anatomy and pulling the filament taught, the naturally curved wall of the coronary sinus can be straightened, whereby to move the posterior mitral annulus anteriorly and thereby reduce mitral regurgitation.

It should also be appreciated that the present invention may also be used to alter the shape of other cardiac tissues, including but not limited to the left ventricle, for other uses, including the treatment of cardiac dysfunction.

It is to be understood that the present invention is by no means limited to the particular constructions herein disclosed and/or shown in the drawings, but also comprises any modifications or equivalents within the scope of the claims.

What is claimed is:

1. A method for reducing mitral regurgitation comprising:
    inserting apparatus into the coronary sinus of a patient in the vicinity of the posterior leaflet of the mitral valve, the apparatus being adapted to move at least a portion of the coronary sinus anteriorly, whereby to move the posterior annulus anteriorly and thereby improve leaflet coaptation, the apparatus comprising a plurality of elements forming a straightening device having a first end and a second end, the straightening device defining a longitudinal axis between the first end and the second end, and the straightening device defining a first side and a second side on opposing sides of the longitudinal axis, the first side defining a series of gaps between the plurality of elements, the straightening device having an insertion configuration comprising orienting the gaps away from the mitral valve so as to allow the straightening device to curve as required to follow a natural curvature of the coronary sinus, the first end configured to allow rotation of the straightening device, the first end having a given length configured to extend outside of the coronary sinus with the second end and the plurality of elements forming the straightening device disposed within the coronary sinus, the straightening device having a straightened configuration wherein the gaps are oriented toward the mitral valve so as to force the straightening device to straighten within the coronary sinus, and wherein the straightening device is configured to rotate within the coronary sinus between the insertion configuration and the straightened configuration, the plurality of elements being separated apart from one another during insertion into the coronary sinus and thereafter closed together in situ so as to form the apparatus; wherein each of the elements has a length such that it is, by itself, insufficient to significantly move the coronary sinus.

2. A method according to claim 1 wherein a distalmost of the elements is fixed to an elongated flexible body.

3. A method according to claim 2 wherein the distalmost of the elements is delivered to the coronary sinus by advancing the flexible body into the coronary sinus.

4. A method according to claim 1 wherein the apparatus is substantially straight along its length.

5. A method according to claim 1 wherein the apparatus is substantially curved along its length.

6. A method according to claim 1 wherein the apparatus is both substantially straight and curved along its length.

7. A method according to claim 1 wherein the elements are inserted into the coronary sinus percutaneously.

8. A method according to claim 7 wherein the elements are inserted into the coronary sinus by introducing the elements into the patient's jugular vein, passing them down the superior vena cava, passing them through the right atrium and then passing them into the coronary sinus.

9. A method according to claim 1 wherein the elements are inserted into the coronary sinus by introducing them into the patient's left subclavian vein, passing them down the superior vena cava, passing them through the right atrium and then passing them into the coronary sinus.

10. A method according to claim 1 wherein the elements are inserted into the coronary sinus through an incision in the patient's heart.

11. A method according to claim 1 wherein the elements are guided into position by passing them through a pre-positioned delivery catheter.

12. A method according to claim 1 wherein the elements are guided into position by passing them over a pre-positioned guidewire.

13. A method according to claim 12 wherein the elements are guided into position by inserting the guidewire into the coronary sinus and then passing the elements down the guidewire.

14. A method according to claim 1 further comprising a subsequent step of removing the apparatus from the coronary sinus.

15. A method according to claim 1 wherein the elements are inserted under visualization.

16. A method according to claim 15 wherein visualization is achieved by using a procedure chosen from the group consisting of fluoroscopy, echocardiography, intravascular ultrasound, angioscopy and real-time magnetic resonance imaging.

17. A method according to claim 1 including an additional step of assessing the efficacy of the procedure.

18. A method for reducing mitral regurgitation comprising:

inserting apparatus into the coronary sinus of a patient in the vicinity of the posterior leaflet of the mitral valve, the apparatus being adapted to move at least a portion of the coronary sinus anteriorly, whereby to move the posterior annulus anteriorly and thereby improve leaflet coaptation, the apparatus comprising a plurality of elements forming a straightening device having a first end and a second end, the straightening device defining a longitudinal axis between the first end and the second end, and the straightening device defining a first side and a second side on opposing sides of the longitudinal axis, the first side defining a series of gaps between the plurality of elements, the straightening device having an insertion configuration comprising orienting the gaps away from the mitral valve so as to allow the straightening device to curve as required to follow a natural curvature of the coronary sinus, the first end configured to allow rotation of the straightening device, the first end having a given length configured to extend outside of the coronary sinus with the second end and the plurality of elements forming the straightening device disposed within the coronary sinus, the straightening device having a straightened configuration wherein the gaps are oriented toward the mitral valve so as to force the straightening device to straighten within the coronary sinus, and wherein the straightening device is configured to rotate within the coronary sinus between the insertion configuration and the straightened configuration, the plurality of elements being separated apart from one another during insertion into the coronary sinus and thereafter closed together in situ so as to form the apparatus; wherein the elements are inserted into the coronary sinus percutaneously; and wherein the elements are guided into position by inserting a guidewire into the coronary sinus, passing the delivery catheter over the guidewire and into the coronary sinus, removing the guidewire, and then passing the elements down the delivery catheter.

19. A method for reducing mitral regurgitation comprising:

inserting apparatus into the coronary sinus of a patient in the vicinity of the posterior leaflet of the mitral valve, the apparatus being adapted to move at least a portion of the coronary sinus anteriorly, whereby to move the posterior annulus anteriorly and thereby improve leaflet coaptation, the apparatus comprising a plurality of elements forming a straightening device having a first end and a second end, the straightening device defining a longitudinal axis between the first end and the second end, and the straightening device defining a first side and a second side on opposing sides of the longitudinal axis, the first side defining a series of gaps between the plurality of elements, the straightening device having an insertion configuration wherein the gaps are orientated away from the mitral valve so as to the allow the straightening device to curve as required to follow a natural curvature of the coronary sinus, the straightening device having a straightened configuration wherein the gaps are oriented toward the mitral valve so as to force the straightening device to straighten within the coronary sinus, and the straightening device is configured to rotate within the coronary sinus between the insertion configuration and the straightened configuration, the plurality of elements being separated apart from one another during insertion into the coronary sinus and thereafter closed together in situ so as to form the straightened configuration;

wherein the elements are guided into position by passing them over a pre-positioned guidewire; and wherein the elements are guided into position by inserting the guidewire into the coronary sinus and then passing the elements down the guidewire.

* * * * *